(12) United States Patent
Szucova et al.

(10) Patent No.: US 7,960,397 B2
(45) Date of Patent: Jun. 14, 2011

(54) 6,9-DISUBSTITUTED PURINE DERIVATIVES AND THEIR USE AS COSMETICS AND COSMETIC COMPOSITIONS

(75) Inventors: Lucie Szucova, Velke Kunetice (CZ); Marek Zatloukal, Sumperk (CZ); Lukas Spichal, Olomouc (CZ); Jiri Voller, Brno-Bystrc (CZ); Karel Dolezal, Olomouc (CZ); Miroslav Strnad, Olomouc (CZ); Frank J. Massino, Napa, CA (US)

(73) Assignee: Institute of Experimental Botany, Academy of Sciences of the Czech Republic, Praha (CZ)

( * ) Notice: Subject to any disclaimer, the term of this patent is extended or adjusted under 35 U.S.C. 154(b) by 649 days.

(21) Appl. No.: 11/966,559

(22) Filed: Dec. 28, 2007

(65) Prior Publication Data
US 2009/0170879 A1 Jul. 2, 2009

(51) Int. Cl.
- *A61P 17/16* (2006.01)
- *A61K 31/52* (2006.01)
- *C07D 473/34* (2006.01)
- *A61P 37/06* (2006.01)

(52) U.S. Cl. ............. 514/263.23; 514/263.4; 514/234.2; 544/118; 544/277

(58) Field of Classification Search ............. 514/263.23, 514/263.4
See application file for complete search history.

(56) References Cited

U.S. PATENT DOCUMENTS
2010/0234401 A1 * 9/2010 Szucova et al. .......... 514/263.23

OTHER PUBLICATIONS
Shadid, Tetrahedron 45(12) 3889 (1989).*
Haidoune, Tet. Letter 1419 (1990).*
Haidoune, J.CHem. Soc. Perkins I, 3009 (1994).*

* cited by examiner

*Primary Examiner* — Mark Berch
(74) *Attorney, Agent, or Firm* — Fitch, Even, Tabin & Flannery

(57) ABSTRACT

Certain 6,9-disubstituted purine derivatives and their pharmaceutically acceptable salts of the following general formula

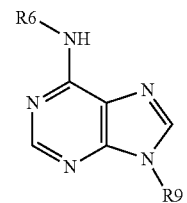

are provided wherein R6 and R9 are as defined in the specification. These 6,9-disubstituted purine derivatives and their pharmaceutically acceptable salts are useful in compositions for application to mammalian cells, and especially human skin cells, in order to improve the cosmetic appearance of the mammalian cells, especially human skin.

14 Claims, No Drawings

6,9-DISUBSTITUTED PURINE DERIVATIVES AND THEIR USE AS COSMETICS AND COSMETIC COMPOSITIONS

TECHNICAL FIELD

The invention relates to 6,9-disubstituted purine derivatives as well as their use as, or in, cosmetics and/or cosmetic preparations.

BACKGROUND

In recent years, 6-substituted aminopurines have assumed considerable biochemical significance. Some compounds of this type promote plant growth and belong to the group of growth regulators termed cytokinins (Letham, Ann. Rev. Plant. Physiol. 18, 349, 1967). In cytokinin bioassays based on induction of cell division in plant tissue cultures, the most active compounds is the naturally occurring cytokinin transzeatin (6-((E)-4-hydroxy-3-methylbut-2-enylamino)purine: Letham, Planta 74:228, 1967). Cytokinins closely related to zeatin occur as bases in soluble RNA (Skoog et al., Science 154:1354, 1966). In the serine and tyrosine RNAs of yeast, plants, and animals the cytokinin is adjacent to the anticodon. The growth of mammalian cell cultures is inhibited by certain $N^6$-substituted adenosines with cytokinin activity (Grace et al., Proc. Am. Assoc. Cancer Res. 8:23, 1967). After the discovery of kinetin (Miller et al., J. Amer. Chem. Soc. 77:1392, 1955), there was a flurry of activity that led to the finding of 6-benzylaminopurine (BA), an active and easily obtainable cytokinin. Much research into cytokinin physiology was subsequently done with this substance.

Alkylation of natural cytokinins at position 9 of the purine nucleus may occur in plants. Lupinic acid, a zeatin conjugated at N9 with the amino acid alanine, was the first detected metabolite of this type (MacLeod et al., J. Org. Chem. 41: 3959, 1976; Duke et al., Phytochemistrry 18:819, 1978; Parker et al., Planta 142:239, 1978). Later, the corresponding 9-alanyl derivative was identified as a metabolite of BA in bean seedlings (Letham et al., Phytochemistry 17:2053, 1979; Zhang et al., J. Plant Growth Regul. 8:181, 1989). Like 9-alanyl zeatin, it exhibited low biological activity and higher stability than the corresponding bases (Parker et al., Planta 142:239, 1978; Palni et al., Planta 160:242, 1984; Zhang et al., J. Plant Growth Regul. 8:181, 1989). The minimisation of BA conjugation has been of both biotechnological and agronomic interest for some time (see, e.g., Zhang et al., J. Plant Growth Regul. 8:181, 1989; Werbrouck et al., Physiol. Plant. 98:291, 1996). 9-Substituted BA derivatives which slowly release free BA may possess enhanced cytokinin activities (e.g., senescence retarding, in vitro morphogenesis, cell division stimulating, etc.) since these compounds are not directly subject to inactivation by conjugation.

A number of 9-substituted cytokinin derivatives have been reported but their structure activity relationships still remain an enigma. The most effective 9-alkyl derivatives developed so far are 9-(2-tetrahydropyranyl)-BA (van Overbeek et al., Science 156:1497, 1967) and 9-(2-tetrahydrofuranyl)-BA (Zhang et al., J. Plant Growth Regul. 8:181, 1989), which both proved to be considerably more active than BA in evoking several growth responses. Since the tetrahydropyranyl group is readily cleaved by acid hydrolysis, it had been suggested that the high biological activity of 9-(2-tetrahydropyranyl)-$N^6$-alkyladenines is probably a consequence of slow cleavage of the 9-substituent (Young et al., Phytochemistry 8:1199, 1969). Subsequently, Fox et al. (Plant Physiol. 47:275, 1971) studied the metabolism of the less active 9-methyl-BA in tobacco and soybean callus tissue and demonstrated rapid conversion to several products. The metabolites were not identified definitively, although it was proposed that conversion to free BA occurred. Pietraface et al., (Physiol. Plant. 53:249, 1981) examined the metabolism of 9-methyl-BA in germinating lettuce seed and suggested formation of BAR and BAR5'P on the basis of chromatographic data. Nevertheless, free BA was not detected. Finally, the application of a 9-(2-tetrahydropyranyl)- and a 9-(2-tetrahydrofuranyl)-BA, assessed for their ability to retard soybean leaf senescence, led to release of free BA (Zhang et al., J. Plant Growth Regul. 8:181, 1989). Both compounds were also debenzylated to adenine substituted with 9-tetrahydropyranyl and 9-tetrahydrofuranyl moiety, respectively. The observed high activity of these 6-benzylamino-9-alkylpurines could be a consequence of their ability to release the free base and to maintain an optimal concentration of the free base over a prolonged period (Zhang et al., J. Plant Growth Regul. 8:181, 1989). Thus, the susceptibility to enzymatic dealkylation is probably the critical factor determining the biological activity of 9-alkyl cytokinins. Hence the less active compounds (Kende et al., Plant Physiol. 43: 1244, 1968; Young et al., Phytochemistry 8:1199, 1969; Corse et al., J. Plant Growth Reg. 8:211, 1989; Motyka et al., SPB Acad Publ., ISBN 90-5103-066-5, p. 215, 1992) are probably not susceptible to cleavage of the 9-substituent and exhibit low or zero activity because of their stability. The enhanced activity of 9-alkyl-BAs relative to those of BA, can be consequently attributed to their ability to gradually release the active free base.

This invention provides growth-regulatory, differentiating, and antisenescent cytokinin analogues having improved selectivity and efficiency index (i.e., that are less toxic yet more efficacious) than analogues known heretofore.

DISCLOSURE OF THE INVENTION

This invention provides 6,9-disubstituted purine derivatives of the general formula I

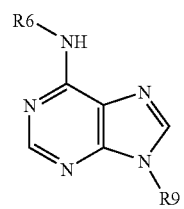

and their pharmaceutically acceptable salts,
wherein R6 is an alkyl, alkenyl, alkynyl, cycloalkyl, aryl, heterocycle, heterocycloalkyl, heteroalkyl, or arylalkyl group containing at least one hydroxyl substitution thereon, and
wherein R9 is a tetrahydropyran-2-yl, tetrahydrofuran-2-yl, 4-chlorobutyl, or 1-ethoxyethyl group;
  wherein alkyl denotes a branched or unbranched alkyl chain containing 1 to 8 carbon atoms, which is optionally substituted independently with 1 to 7 substituents selected from the group containing hydroxyl, halogen, alkyloxy, aryloxy, alkylamino, arylamino, amino, mercapto, carboxyl, cyano, nitro, carbamoyl, sulpho, sulphamido, acylamino, acyloxy, alkylthio, arylthio, cycloalkyl, alkyloxycarbonylamino, aryloxycarbonylamino, aryl, heterocycle and heteroaryl group;
  wherein alkenyl denotes a branched or unbranched alkenyl chain containing 2 to 7 carbon atoms with at least one double bond therein (e.g., vinyl, allyl, 1-propenyl, 1-methylethenyl, but-1 to 3-enyl, pent-1 to 4-enyl, hex-1 to 5-enyl, hept-1 to 6-enyl, allyl, isopentenyl, dimethylallyl) being optionally substituted independently with 1 to 6 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group, wherein alkynyl denotes a branched or unbranched alkynyl chain containing 2 to 7 carbon atoms with at least one triple bond therein (e.g., ethynyl, propargyl, methylethynyl, but-1 to 3-ynyl, pent-1 to 4-ynyl, hex-1 to 5-ynyl, hept-1 to 6-ynyl) being optionally substituted independently with 1 to 6 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, alkyloxycarbonylamino, and aryloxycarbonylamino group;

wherein cycloalkyl denotes a monocyclic or polycyclic alkyl group containing 3 to 15 carbon atoms (e.g., cyclopropyl, cyclobutyl, cyclopentyl, cyclohexyl, cycloheptyl, or adamantyl) being optionally substituted independently with 1 to 7 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl aryloxycarbonylamino, and alkyloxycarbonylamino group;

wherein aryl denotes an aromatic carbocyclic group containing 6 to 18 carbon atoms with at least one aromatic ring or a multiple condensed ring with at least one aromatic ring (e.g., phenyl, biphenyl, naphthyl, tetrahydronaphtyl, fluorenyl, indenyl, phenanthrenyl, 1,2,3,4-tetrahydronaphtyl, naphtyl, anthryl, or phenantryl), which is optionally substituted independently with 1 to 7 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein heterocycle denotes a heterocyclic group containing 4 to 9 carbon atoms and at least one heteroatom selected from the group containing oxygen atom, sulphur atom, and nitrogen atom (e.g., thienyl, furyl, pyranyl, pyrrolyl, imidazolyl, pyrrazolyl, pyridyl, pyrazinyl, pyrimidinyl, pyridazinyl, isothiazolyl, isoxazyl, benzothienyl, naphthothienyl, benzofuranyl, chromenyl, indolyl, isoindolyl, indazolyl, quinolyl, isoquinolyl, phtalazinyl, quinoxalinyl, cinnolinyl, or quinazolinyl), which is optionally substituted independently with 1 to 7 substituents selected from the group containing alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroaryl denotes a heterocycle in which at least one heterocyclic ring is aromatic which is optionally substituted independently with 1 to 7 substituents selected from the group containing alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heterocycloalkyl denotes a —$R_a$-Het group where Het is a heterocycle group and $R_a$ is an alkyl group which can be optionally substituted independently with 1 to 7 substituents selected from the group containing alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroarylalkyl denotes a —$R_a$-HetAr group where HetAr is an heteroaryl group and $R_a$ is as defined above;

wherein arylalkyl denotes a —$R_b$—Ar group where Ar is aryl group and $R_b$ is a branched or unbranched alkyl chain containing 1 to 6 carbon atoms, the aryl group being substituted independently with 1 to 5 substituents selected from the group containing alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein halogen denotes a fluorine, bromine, chlorine, or iodine atom, wherein hydroxy denotes an —OH group, wherein mercapto denotes a —SH group, wherein amino denotes a —$NH_2$ group, wherein carbamoyl denotes a —$CONH_2$ group, wherein cyano denotes a —CN group, wherein carboxyl denotes a —COOH group, wherein nitro denotes a —$NO_2$ group, wherein sulpho denotes a —$SO_3R_c$ group where $R_c$ is hydrogen or alkyl, wherein sulphamido denotes the $SO_2NR_cR_c'$ group where $R_c$ and $R_c'$ are independently hydrogen or alkyl, wherein acyl denotes a —$C(O)R_d$ group, wherein $R_d$ is alkyl, aryl, arylalkyl or cycloalkyl, wherein acyloxy denotes a —O—$C(O)R_e$ group where $R_e$ is alkyl, aryl, or heterocycle, wherein acylamino denotes a —$NHCOR_f$ group, wherein $R_f$ is alkyl, heterocycle, or aryl, wherein alkyloxycarbonylamino denotes a —$NHCOOR_g$ group where $R_g$ is alkyl or cycloalkyl, wherein aryloxycarbonylamino denotes a —$NHCOOR_h$ group where $R_h$ is aryl, wherein alkyloxy denotes a —$OR_h$ group where $R_h$ is alkyl, cycloalkyl, or arylalkyl, wherein aryloxy denotes a —$OR_g$ group where $R_g$ is aryl, wherein alkylamino denotes a —$NR_iR_j$ group where $R_i$ is hydrogen, alkyl, or heterocycle and $R_j$ is alkyl or heterocycle, wherein arylamino denotes a —$NR_kR_h$ group where $R_k$ is hydrogen or aryl and $R_h$ is alkyl, aryl, or heterocycle, wherein alkylthio denotes a —$SR_h$ group where $R_h$ is as defined above, and wherein arylthio denotes a —$SR_g$ group where $R_g$ is as defined above.

Preferred 6,9-disubstituted purine derivatives include 6-(2-hydroxycyclopropylamino)-9-(tetrahydropyran-2-yl, tetrahydrofuran-2-yl, 4-chlorobutyl, 1-ethoxyethyl)purine, 6-(3-hydroxycyclobutylamino)-9-(tetrahydropyran-2-yl, tetrahydrofuran-2-yl, 4-chlorobutyl, 1-ethoxyethyl)purine, 6-(4-hydroxycyclohexylamino)-9-(tetrahydropyran-2-yl, tetrahydrofuran-2-yl, 4-chlorobutyl, 1-ethoxyethyl)purine, 6-(2-hydroxy-3-chlorobenzylamino)-9-(tetrahydropyran-2- yl, tetrahydrofuran-2-yl, 4-chlorobutyl, 1-ethoxyethyl)purine, 6-(4-hydroxy-3-chlorobenzylamino)-9-(tetrahydropyran-2-yl, tetrahydrofuran-2-yl, 4-chlorobutyl, 1-ethoxyethyl)purine, 6-(3-hydroxy-4-chlorobenzylamino)-9-(tetrahydropyran-2-yl, tetrahydrofuran-2-yl, 4-chlorobutyl, 1-ethoxyethyl)purine, 6-(2-hydroxy-3-iodobenzylamino)-9-(tetrahydropyran-2-yl, tetrahydrofuran-2-yl, 4-chlorobutyl, 1-ethoxyethyl)purine, 6-(4-hydroxy-5-iodobenzylamino)-9-(tetrahydropyran-2-yl, tetrahydrofuran-2-yl, 4-chlorobutyl, 1-ethoxyethyl)purine, 6-(3-hydroxy-4-iodobenzylamino)-9-(tetrahydropyran-2-yl, tetrahydrofuran-2-yl, 4-chlorobutyl, 1-ethoxyethyl)purine, 6-(2-hydroxy-3-bromobenzylamino)-9-(tetrahydropyran-2-yl, tetrahydrofuran-2-yl, 4-chlorobutyl, 1-ethoxyethyl)purine, 6-(4-hydroxy-3-bromobenzylamino)-9-(tetrahydropyran-2-yl, tetrahydrofuran-2-yl, 4-chlorobutyl, 1-ethoxyethyl)purine, 6-(3-hydroxy-4-bromobenzylamino)-9-(tetrahydropyran-2-yl, tetrahydrofuran-2-yl, 4-chlorobutyl, 1-ethoxyethyl)purine, 6-(2-hydroxy-3-fluorobenzylamino)-9-(tetrahydropyran-2-yl, tetrahydrofuran-2-yl, 4-chlorobutyl, 1-ethoxyethyl)purine, 6-(4-hydroxy-3-fluorobenzylamino)-9-(tetrahydropyran-2-yl, tetrahydrofuran-2-yl, 4-chlorobutyl, 1-ethoxyethyl)purine, 6-(3-hydroxy-4-fluorobenzylamino)-9-(tetrahydropyran-2-yl, tetrahydrofuran-2-yl, 4-chlorobutyl, 1-ethoxyethyl)purine, 6-(2,3-dihydroxy-4-methoxybenzylamino)-9-(tetrahydropyran-2-yl, tetrahydrofuran-2-yl, 4-chlorobutyl, 1-ethoxyethyl)purine, 6-(2,4-dihydroxy-3-methoxybenzylamino)-9-(tetrahydropyran-2-yl, tetrahydrofuran-2-yl, 4-chlorobutyl, 1-ethoxyethyl)purine, 6-(2,5-dihydroxy-4-methoxybenzylamino)-9-(tetrahydropyran-2-yl, tetrahydrofuran-2-yl, 4-chlorobutyl, 1-ethoxyethyl)purine, 6-(3,5-dihydroxy-4-chlorobenzylamino)-9-(tetrahydropyran-2-yl, tetrahydrofuran-2-yl, 4-chlorobutyl, 1-ethoxyethyl)purine, 6-(2-hydroxybenzylamino)-9-(tetrahydropyran-2-yl, tetrahydrofuran-2-yl, 4-chlorobutyl, 1-ethoxyethyl)purine, 6-(3-hydroxybenzylamino)-9-(tetrahydropyran-2-yl, tetrahydrofuran-2-yl, 4-chlorobutyl, 1-ethoxyethyl)purine, 6-(4-hydroxybenzylamino)-9-(tetrahydropyran-2-yl, tetrahydrofuran-2-yl, 4-chlorobutyl, 1-ethoxyethyl)purine, 6-(3-hydroxy-4-methoxybenzylamino)-9-(tetrahydropyran-2-yl, tetrahydrofuran-2-yl, 4-chlorobutyl, 1-ethoxyethyl)purine, 6-(3-hydroxy-5-methoxybenzylamino)-9-(tetrahydropyran-2-yl, tetrahydrofuran-2-yl, 4-chlorobutyl, 1-ethoxyethyl)purine, 6-(2-hydroxy-3-methoxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(2-hydroxy-4-methoxybenzylamino)-9-(tetrahydropyran-2-yl, tetrahydrofuran-2-yl, 4-chlorobutyl, 1-ethoxyethyl)purine, 6-(4-hydroxy-2-methoxybenzylamino)-9-(tetrahydropyran-2-yl, tetrahydrofuran-2-yl, 4-chlorobutyl, 1-ethoxyethyl)purine, 6-(3,5-dimethyl-4-hydroxybenzylamino)-9-(tetrahydropyran-2-yl, tetrahydrofuran-2-yl, 4-chlorobutyl, 1-ethoxyethyl)purine, 6-(3,5-dibromo-4-hydroxybenzylamino)-9-(tetrahydropyran-2-yl, tetrahydrofuran-2-yl, 4-chlorobutyl, 1-ethoxyethyl)purine, 4-chlorobutyl, 1-ethoxyethyl)purine, 6-(3-hydroxymethyl-3-methylallyl)amino)-9-(tetrahydropyran-2-yl, tetrahydrofuran-2-yl, 4-chlorobutyl, 1-ethoxyethyl)purine, 6-(Z)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(Z)-(1'-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1'-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(2-hydroxy-3-pyridylamino)-9-(tetrahydropyran-2-yl, tetrahydrofuran-2-yl, 4-chlorobutyl, 1-ethoxyethyl)purine, 6-(3-hydroxy-4-pyridylamino)-9-(tetrahydropyran-2-yl, tetrahydrofuran-2-yl, 4-chlorobutyl, 1-ethoxyethyl)purine, 6-(2-hydroxy-4-morfolinylamino)-9-(tetrahydropyran-2-yl, tetrahydrofuran-2-yl, 4-chlorobutyl, 1-ethoxyethyl)purine, 6-(3-hydroxy-1-pyrolidinylamino)-9-(tetrahydropyran-2-yl, tetrahydrofuran-2-yl, 4-chlorobutyl, 1-ethoxyethyl)purine, 6-(4-hydroxy-2-methylanilino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-6-methylanilino)-9-(tetrahydropyran-2-yl, tetrahydrofuran-2-yl, 4-chlorobutyl, 1-ethoxyethyl)purine, 6-(3-carboxy-4-hydroxyanilino)-9-(tetrahydropyran-2-yl, tetrahydrofuran-2-yl, 4-chlorobutyl, 1-ethoxyethyl)purine, 6-(4-hydroxy-2-methoxyanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine and their pharmaceutically acceptable salts.

Particularly preferred 6,9-disubstituted purine derivatives include 6-(4-hydroxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1'-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, 4-chlorobutyl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine, and their pharmaceutically acceptable salts.

Another aspect of the invention are the 6,9-disubstituted purine derivatives of general formula I for use as cosmetics for inhibiting ageing and senescence of mammalian cells, especially epidermal cells such as keratinocytes or fibroblasts.

A further aspect of the invention are the 6,9-disubstituted purine derivatives of the general formula I for treating skin disease states (e.g., lupus, allergic eczema, toxic eczema, atopic dermatitis, ichtyosis, papilloma, Bowen's disease, seborrhoic keratosis, actinic keratosis, basal and squamous cell carcinoma, and the like).

Another aspect of the invention are the 6,9-disubstituted purine derivatives of the general formula I for treating inflammation, treating or accelerating the healing of lesions, and providing substantially immediate relief of pain and/or other immunological responses resulting from inflammation.

In a preferred embodiment, the 6,9-disubstituted purine derivatives of the general formula I are used for treating inflammation skin diseases as atopic dermatitis, lichen planus, hyperpigmentation, and Herpes simplex lesions.

The present invention provides a composition comprising one or more 6,9-disubstituted purine derivatives of the general formula I or their pharmaceutically acceptable salts thereof; especially preferred pharmaceutically acceptable salts are formed with alkali metals, ammonium or amines and may be in the forms of racemates, optically active isomers, or their addition salts with acids. Such compositions may contain other components so long as they are acceptable for application to mammalia cells and do not adversely effect or interfere with the activities of the one or more 6,9-disubstituted purine derivatives; these components can include, but are not limited to, one or more excipients and/or ingredients normally used in cosmetic products.

A further aspect of the invention is the composition comprising one or more 6,9-disubstituted purine derivatives of the general formula I or the pharmaceutically acceptable salts thereof with alkali metals, ammonium or amines, in the forms of racemates or optically active isomers, or their addition salts with acids, and one or more excipients destined for inhibiting ageing and senescence of mammalian epidermal cells, such as keratinocytes or fibroblasts.

A further aspect of the invention is the composition comprising one or more 6,9-disubstituted purine derivatives of the general formula I or the pharmaceutically acceptable salts thereof with alkali metals, ammonium or amines, in the forms of racemates or optically active isomers, or their addition salts with acids, and one or more excipients destined for treating skin disease states.

In a preferred embodiment, the object of the invention is the composition comprising one or more 6,9-disubstituted purine derivatives of the general formula I or the pharmaceutically acceptable salts thereof with alkali metals, ammonium or amines, in the forms of racemates or optically active isomers, or their addition salts with acids, and one or more excipients, destined for treating lupus, allergic eczema, toxic eczema, atopic dermatitis, ichtyosis, papilloma, Bowen's disease, seborrhoic keratosis, actinic keratosis, basal and squamous cell carcinoma.

Another aspect of the invention is the composition comprising one or more 6,9-disubstituted purine derivatives of the general formula I or the pharmaceutically acceptable salts thereof with alkali metals, ammonium or amines, in the forms of racemates or optically active isomers, or their addition salts with acids, and one or more excipients destined for treating the inflammation, to accelerate healing of lesions, and to provide substantially immediate relief of pain and other immunological responses resulting from inflammation.

The compositions of the present invention are useful for inhibiting ageing and/or senescence, improving the cosmetic appearance of mammalian cells (especially epidermal cells such as keratinocytes or fibroblasts) and/or mammalian skin, and/or ameliorating the adverse effect of aging in mammalian cells (especially epidermal cells such as keratinocytes or fibroblasts). For purposes of this invention, "inhibiting" is intended to include slowing, reversing, or stopping the development of undesirable cosmetic features, or otherwise improving the cosmetic appearance. These compositions are particularly useful for inhibiting ageing and senescence and/or improving the cosmetic appearance of human epidermal cells and/or human skin.

The compositions of the present invention are also useful for treatment of certain skin disease states, such as lupus, allergic eczema, toxic eczema, atopic dermatitis, ichtyosis, papilloma, Bowen's disease, seborrhoic keratosis, actinic keratosis, basal and squamous cell carcinoma, and the like.

The compositions of the present invention are also useful for treating inflammation-related conditions, such as inflammation, lesions (e.g., accelerating healing thereof), pain and/or other immunological responses resulting from, or related to, inflammation (e.g., providing relief thereof) and/or treating inflammation skin diseases (e.g., atopic dermatitis, lichen planus, hyperpigmentation, Herpes simplex lesions, and the like).

The present invention further provides a method for ameliorating the adverse effect of aging in mammalian cells (especially epidermal cells such as keratinocytes or fibroblasts), said method comprising applying an effective amount of a novel 6,9-disubstituted purine derivative of this invention to the mammalian cells. Topically application to human skin is an especially preferred embodiment.

The present invention further provides a method for treating disease states in a mammal, said method comprising applying an effective amount of a novel 6,9-disubstituted purine derivative of this invention to the mammalian cells.

The present invention further provides a method for treating an inflammation condition in mammal, said method comprising applying an effective amount of a novel 6,9-disubstituted purine derivative of this invention to mammalian cells.

COMPOSITIONS. The cosmetic compositions of this invention generally comprise from about 0.05% (w/w) to about 10% (w/w) of the active ingredient (i.e., one or more 6,9-disubstituted purine derivatives as described herein), preferably from about 0.1% (w/w) to about 2% (w/w). The cosmetic compositions can be in the form of a cream, an aerosol, a milky lotion, a lotion, a plaster, a poultice, a shampoo, a lipstick, an ointment, a paste, foam, a tincture, a spray, or the like.

Ointments are oil-in-water emulsions, which comprise not more than 70%, but preferably 20-50% of water or aqueous phase. The fatty phase consists of, in particular, hydrocarbons, for example vaseline, paraffin oil or hard paraffins, which preferably comprise suitable hydroxy compounds, such as fatty alcohols or esters thereof, for example cetyl alcohol or wool wax alcohols, such as wool wax, to improve the water-binding capacity. Emulsifiers are lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Fatty ointments are anhydrous and comprise, as the base, in particular, hydrocarbons, for example paraffin, vaseline or paraffin oil, and furthermore naturally occurring or semi-synthetic fats, for example hydrogenated coconut-fatty acid triglycerides, or, preferably, hydrogenated oils, for example hydrogenated groundnut or castor oil, and furthermore fatty acid partial esters of glycerol, for example glycerol mono- and/or distearate, and for example, fatty alcohols. They also contain emulsifiers and/or additives mentioned in connection with the ointments which increase the uptake of water.

Creams are oil-in-water emulsions, which comprise more than 50% of water. Oily bases used are, in particular, fatty alcohols, for example lauryl, cetyl or stearyl alcohols, fatty acids, for example palmitic or stearic acid, liquid to solid waxes, for example isopropyl myristate, wool wax or beeswax, and/or hydrocarbons, for example vaseline (petrolatum) or paraffin oil. Emulsifiers are surface-active substances with predominantly hydrophilic properties, such as non-ionic emulsifiers, for example fatty acid esters of polyalcohols or ethyleneoxy adducts thereof, such as polyglyceric fatty acid esters or polyethylene sorbitan fatty esters (Tweens), and furthermore polyoxyethylene fatty alcohol ethers or polyoxyethylene fatty acid esters, or ionic emulsifiers, such as alkali metal salts of fatty alcohol sulphates, for example sodium lauryl sulphate, sodium cetyl sulphate or sodium stearyl sulphate, which are usually used in the presence of fatty alcohols, for example cetyl stearyl alcohol or stearyl alcohol. Additives to the aqueous phase are, inter alia, agents which prevent the creams from drying out, for example polyalcohols, such as glycerol, sorbitol, propylene glycol and/or polyethylene glycols, and furthermore preservatives and odoriferous substances.

Pastes are creams and ointments containing secretion-absorbing powder constituents, such as metal oxides, for example titanium oxide or zinc oxide, and in addition talc and/or aluminium silicates, which have the task of binding the moisture or secretions present.

Suspensions in oil comprise, as the oily component, the vegetable, synthetic or semisynthetic oils. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are therefore, for example: ethyl oleate, isopropyl myristate, isopropyl palmitate, "Labrafil™ M 2375" (polyoxyethylene glycerol trioleate from Gattefosé, Paris), "Labrafil™ M 1944 CS" (unsaturated polyglycolated glycerides prepared by an alcoholysis of apricot kernel oil and made up of glycerides and polyethylene glycol esters; from Gattefosé, Paris), "Labrasol™" (saturated polyglycolated glycerides prepared by an alcoholysis of TCM and made up of glycerides and polyethylene glycol esters; from Gattefosé, Paris) and/or "Miglyol™ 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

Foams are administered from pressurised containers and they are liquid oil-in-water emulsions present in aerosol foam. As the propellant gases halogenated hydrocarbons, such as polyhalogenated alkanes, for example dichlorofluoromethane and dichlorotetrafluoroethane, or, preferably, nonhalogenated gaseous hydrocarbons, air, $N_2O$, or carbon dioxide are used. The oily phases used are, inter alia, those mentioned above for ointments and creams, and the additives mentioned there are likewise used.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e., lipophilic substances soluble in the aqueous mixture to substitute the fatty substances removed from the skin with the ethanol, and, if necessary, other excipients and additives are admixed.

The invention also relates to a process or method for the treatment of the cell senescence and the disease states mentioned above. The compounds can be administered prophylactically or therapeutically in the form of cosmetic compositions, preferably in an amount which is effective against the cell senescence or the disease states mentioned.

EXAMPLES

The invention is further illustrated by the following examples, which should not be construed as further limiting. Compounds not falling within general formula I are included in the Examples for comparison purposes.

The starting material for the compounds of the formula I is 6-chloro-9-(tetrahydropyran-2-yl)purine, synthesised from 6-chloropurine and 3,4-dihydopyran using p-toluenesulfonic acid according to the literature (Robins et al., J. Am. Chem. Soc. 83, 2574 (1961)). Starting substituted benzylamines, not commercially available (otherwise obtained via Sigma Aldrich or Fluorochem), were prepared from the corresponding aldehydes in the presence of a suitable metal catalyst. 3-Methyl-but-2-enylamine was prepared by a three-step synthesis from the corresponding halide using the Gabriel synthesis. 4-Hydroxy-3-methyl-E-but-2-enyl-amine was prepared by a five-step synthesis from isoprene according to the literature (Ohsugi et al., Agr. Biol. Chem., 38 (10), 1925, (1974)).

Elemental analyses (C, H and N) were performed on the EA1108 CHN analyser (Fissons Instruments). The melting points were determined on the BÜCHI Melting Point B-540 apparatus and are uncorrected. Analytical thin layer chromatography (TLC) was carried out using silica gel 60 $WF_{254}$ plates (Merck), solvent $CHCl_3$:MEOH:conc. $NH_4OH$ (8:2: 0.2, v/v/v). ES+ mass spectra were recorded using direct probe on the Waters ZMD 2000 mass spectrometer. The mass monitoring interval was 10-1500 amu. The spectra were collected using 3.0 second cyclic scans and applying a sample cone voltage of 25 V at source block temperature 150° C., desolvation temperature 80° C. and desolvation gas flow rate 200 l/hour. The mass spectrometer was directly coupled to a MassLynx data system. NMR spectra were measured on the Bruker Avance AV 300 spectrometer operating at a temperature of 300 K and a frequency of 300.13 MHz ($^1H$) and 75.48 MHz ($^{13}C$), respectively. Samples were prepared by dissolving the compounds in DMSO-$d_6$. Tetramethylsilane (TMS) was used as the internal standard.

Example 1

6-(4-hydroxybenzylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (1478 mg) 4-hydroxybenzylamine, and 5 mL of triethylamine was refluxed in n-propanol for 3 hours. After removal of the n-propanol by vacuum evaporation, the resulting material was treated with water and extracted into ethyl acetate. The ethyl acetate solvent was evaporated and the residuum subsequently washed with 30 ml of diethylether. The solid residue was filtered off and the crude product crystallized from methanol. Yield 80%, white solid. TLC (EtOAc:hexane (1:1) (v:v): single spot; HPLC: purity >98%. $^1$H-NMR (400 MHZ, DMSO): 1.57tt (2H, $J_a$=11.0 Hz, $J_b$=3.3 Hz); 1.72qq (1H, $J_a$=12 Hz, $J_b$=3.3 Hz); 1.95tt (2H, $J_a$=11 Hz, $J_b$=2.1 Hz); 2.27qq (1H, $J_a$=12.0 Hz, $J_b$=3.3 Hz); 3.67m (1H); 4.0dd (1H, $J_a$=11.0 Hz, $J_b$=2.1 Hz); 4.6s (2H); 5.63dd (1H, $J_a$=11.0 Hz, $J_b$=2.1 Hz); 6.67d (2H, J=8.4Hz); 7.15d (2H, J=8.4 Hz); 8.02bs (1H); 8.21s (1H); 8.33s (1H); 9.21s (1H). MS (ES): $[M+H]^+$=326 (100).

Example 2

6-(3-hydroxybenzylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (1478 mg) 3-hydroxybenzylamine, and 5 mL of triethylamine was refluxed in n-butanol for 3 hours. After removal of the n-butanol by vacuum evaporation water was added to remove the n-butanol residues. The resulting material was treated with water and partitioned into ethyl acetate. The ethyl acetate phase was evaporated and the residuum subsequently washed with 30 ml of diethylether. The solid residue was filtered off and the crude product crystallized from methanol. Yield 90%, white solid. TLC (EtOAc: hexane (1:1) (v:v): single spot; HPLC: purity >99%. $^1$H-NMR (400 MHZ, DMSO): 1.57m (2H); 1.70m (1H); 1.95m (2H); 2.27qq (1H, $J_a$=11.7 Hz, $J_b$=4.0 Hz); 3.66m (1H); 4.0d (1H); 4.63bs (2H); 5.67dd (1H, $J_a$=11.3 Hz, $J_b$=1.8 Hz); 6.58dd (1H, $J_a$=8.2 Hz, $J_b$=1.5 Hz); 6.73 (d, 1H, J=7.7 Hz); 7.07t (1H, J=7.7 Hz); 8.21 s (1H); 8.33bs (1H); 8.36bs (1H); 9.26 (1H). MS (ES): [M+H]$^+$=326 (100).

Example 3

6-(2-hydroxybenzylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (1478 mg) 2-hydroxybenzylamine, and 5 mL of triethylamine was refluxed in n-propanol for 3 hrs. After removal of the n-propanol by vacuum evaporation, the resulting material was treated with water and extracted into ethyl acetate. The ethyl acetate solvent was evaporated and the residuum subsequently washed with 30 ml of diethylether. The solid residue was filtered off and the crude product crystallized from methanol. Yield 90%, white solid. TLC (EtOAc:hexane (1:1) (v:v): single spot; HPLC: purity >98%. $^1$H-NMR (400 MHZ, DMSO): 1.58m (2H); 1.70m (1H); 1.95m (2H); 2.26qq (1H, $J_a$=11.8 Hz, $J_b$=4.0 Hz); 3.67m (1H); 4.0d (1H, J=11.3 Hz); 4.64bs (2H); 5.63dd (1H, $J_a$=11.3 Hz, $J_b$=1.8 Hz); 6.73t (1H, J=7.5 Hz); 6.82 (d, 1H, J=7.9 Hz); 7.06t (1H, J=7.5 Hz); 7.14d (1H, J=7.5 Hz); 8.21 s (1H); 8.35bs (1H); 8.37bs (1H); 9.82bs (1H). MS (ES): [M+H]$^+$=326 (100).

Example 4

6-(2,3-dihydroxybenzylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (2100 mg) 2,3dihydroxybenzylamine hydrochloride, and 7 mL of triethylamine was refluxed in n-propanol for 3 hrs. After removal of the n-propanol by vacuum evaporation, the resulting material was treated with water and extracted into ethyl acetate. The ethyl acetate solvent was evaporated and the residuum subsequently washed with 30 ml of petroleum ether. The solid residue was filtered off and the crude product crystallized from methanol. Yield 60%, white solid. TLC (CHCl$_3$:methanol) (4:1) (v:v): single spot; HPLC: purity >98%. $^1$H-NMR (300 MHz, DMSO): 1.57m (2H); 1.71m (1H); 1.95m (2H); 2.27qq (1H, $J_a$=12 Hz, $J_b$=4.0 Hz); 3.67m (1H); 4.00d (1H, J=11.7 Hz); 4.58bs (2H); 5.63dd (1H, $J_a$=11.2 Hz, $J_b$=1.9 Hz); 6.55tt (1H, $J_a$=7.7 Hz, $J_b$=1.5 Hz); 6.63dd (1H, $J_a$=7.7 Hz, $J_b$=1.8 Hz); 6.66dd (1H, $J_a$=7.7 Hz, $J_b$=1.8 Hz); 8.24s (1H); 8.27bs (1H); 8.37s (1H), 8.96bs (1H), 9.53bs (1H). MS (ES): [M+H]$^+$=342 (100).

Example 5

6-(E)-(4-hydroxy-3-methylbut-2-en-1-ylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (1754 mg) (E)-(4-hydroxy-3-methylbut-2-en-1-ylamine hemioxalate and 3 mL of triethylamine was refluxed in n-butanol for 3 hrs. After removal of the n-butanol by vacuum evaporation, the resulting material was treated with water and extracted into ethyl acetate. The ethyl acetate phase was evaporated and the residuum subsequently washed with 30 ml of diethylether. The solid residue was filtered off and the crude product crystallized from methanol. Yield 75%, white solid. TLC (CHCl$_3$: methanol (4:1) (v:v): single spot; HPLC: purity >98%. $^1$H-NMR (400 MHz, DMSO): 1.36m (2H); 1.66s (3H); 1.71m (1H); 1.94m (2H); 2.25m (1H); 3.67m (1H); 3.78d (2H, J=5.7 Hz); 4.00 d)1H, J=10.8 Hz); 4.14bs (2H); 4.71t (1H, J=5.7 Hz); 5.52t (1H, J=6.0 Hz); 5.61dd (1H, $J_a$=10.8 Hz, $J_b$=2.0 Hz); 7.83bs (1H); 8.21s (1H); 8.31bs (1H). MS (ES): [M+H]$^+$=304 (100).

Example 6

6-(4-hydroxy-3-methylbutylamino)-9-(tetrahydropyran-2-yl)purine. A mixture of 10 mmol (2387 mg) 6-chloro-9-(tetrahydropyran-2-yl)purine (prepared from 10 mmol (1546 mg) of 6-chloropurine), 12 mmol (2318 mg) 4-hydroxy-3-methylbutylamine oxalate, and 5 mL of triethylamine was refluxed in n-propanol for 3 hours and subsequently 24 hrs at laboratory temperature. After removal of the n-propanol by vacuum evaporation, the resulting material was treated with water and partitioned into ethyl acetate. The ethyl acetate phase was evaporated and the residuum subsequently washed with 30 ml of hexane. The solid residue was filtered off and the crude product crystallized from methanol. Yield 75%, white solid. TLC (CHCl$_3$:methanol (4:1) (v:v): single spot; HPLC: purity >98%. $^1$H-NMR (400 MHz, DMSO): 0.88d (3H, J=6.6 Hz); 1.34m (1H); 1.56m (3H); 1.70m (1H); 1.71m (1H); 1.93m (2H); 1.94m (1H); 2.26m (1H); 3.25m (1H); 3.52bs (2H); 3.67m (1H); 4.0d (1H, J=11.3 Hz); 4.42t (1H, J=5.1 Hz); 5.61d (1H, J=10.6 Hz); 7.70bs (1H); 8.20s (1H); 8.30s (1H). MS (ES): [M+H]$^+$=306 (100).

Example 7

6-(4-hydroxyanilino)-9-(tetrahydropyran-2-yl)-purine. A mixture of 10 mmol (2387 mg) 6-chloro-9-(tetrahydropyran-2-yl)purine (prepared from 10 mmol (1546 mg) of 6-chloropurine), 12 mmol (1309 mg) of 4-hydroxyphenylamine (4-hydroxyaniline) and 4 ml of N-ethyldiisopropylamine was refluxed in n-butanol for 3 hrs. After removal of the n-butanol by vacuum evaporation, the resulting material was treated with water and extracted into ethyl acetate. The ethyl acetate solvent was evaporated and the residuum subsequently washed with 30 ml of ether. The solid residue was filtered off and the crude product crystallized from methanol. Yield: 90%, white solid. TLC (CHCl$_3$:CH$_3$OH:NH$_3$) (90:10:0.1) (v:v): single spot; HPLC: purity >98%. $^1$H NMR (400 MHz, DMSO): 1.56tt (2H, $J_a$=11.0 Hz, $J_b$=3.3 Hz); 1.72qq (1H, $J_a$=11.6 Hz, $J_b$=3.3 Hz); 1.94tt (2H, $J_a$=11.0 Hz, $J_b$=3.3 Hz); 2.28qq (1H, $J_a$=11.6 Hz, $J_b$=3.3 Hz); 3.66m (1H); 3.98dd ($^1$H, $J_a$=11.0 Hz, $J_b$=2.1 Hz); 5.62dd (1H, $J_a$=11.0 Hz, $J_b$=2.1 Hz); 7.02d (2H, J=8.5 Hz); 8.19s (1H); 8.26d (2H, J=8.5 Hz); 8.29s (1H); 8.95s (1H). MS (ES$^+$): [M+H]$^+$=312 (100).

TABLE 1

Compounds prepared by the method of examples 1-7

| | PURINE SUBSTITUENT | | CHN ANALYSES | MS ANALYSES-ZMD | |
|---|---|---|---|---|---|
| | R6 | R9 | [%] | [M − H]⁻ a) | [M + H]⁺ b) |
| 1 | (E)-(4-hydroxy-2-methylbut-2-en-1-ylamino) | tetrahydropyran-2-yl | C = 59.0; H = 6.7; N = 23.6 | 302 | 304 |
| 2 | (Z)-(4-hydroxy-3-methylbut-2-en-1-ylamino) | tetrahydropyran-2-yl | C = 59.8; H = 6.9; N = 23.5 | 302 | 304 |
| 3 | (E)-(4-hydroxy-3-methylbut-2-en-1-ylamino) | tetrahydropyran-2-yl | C = 59.6; H = 6.9; N = 22.8 | 302 | 304 |
| 4 | (Z)-(4-hydroxy-1,3-dimethylbut-2-en-1-ylamino) | tetrahydropyran-2-yl | C = 60.0; H = 7.4; N = 22.4 | 316 | 318 |
| 5 | (E)-(4-hydroxy-1,3-dimethylbut-2-en-1-ylamino) | tetrahydropyran-2-yl | C = 60.4; H = 7.5; N = 22.4 | 316 | 318 |
| 6 | 4-hydroxy-3-methylbutylamino | tetrahydropyran-2-yl | C = 58.9; H = 7.5; N = 23.0 | 304 | 306 |
| 7 | 4-hydroxybut-2-en-1-ylamino | tetrahydropyran-2-yl | C = 58.1; H = 6.6; N = 24.2 | 288 | 290 |
| 8 | 2-hydroxybenzylamino | tetrahydropyran-2-yl | C = 62.4; H = 5.9; N = 21.3 | 324 | 326 |
| 9 | 3-hydroxybenzylamino | tetrahydropyran-2-yl | C = 62.8; H = 5.9; N = 21.3 | 324 | 326 |
| 10 | 4-hydroxybenzylamino | tetrahydropyran-2-yl | C = 62.7; H = 5.8; N = 21.6 | 324 | 326 |
| 11 | 2-hydroxy-3-methoxybenzylamino | tetrahydropyran-2-yl | C = 63.6; H = 6.3; N = 20.2 | 354 | 356 |
| 12 | 2-hydroxy-4-methoxybenzylamino | tetrahydropyran-2-yl | C = 63.6; H = 6.3; N = 20.3 | 354 | 356 |
| 13 | 2-hydroxy-5-methoxybenzylamino | tetrahydropyran-2-yl | C = 63.6; H = 6.3; N = 20.2 | 354 | 356 |
| 14 | 2,3-dihydroxybenzylamino | tetrahydropyran-2-yl | C = 59.9; H = 5.7; N = 20.7 | 340 | 342 |
| 15 | 2,4-dihydroxybenzylamino | tetrahydropyran-2-yl | C = 59.7; H = 5.6; N = 20.5 | 340 | 342 |
| 16 | 2,5-dihydroxybenzylamino | tetrahydropyran-2-yl | C = 60.0; H = 5.7; N = 20.6 | 340 | 342 |
| 17 | 2,6-dihydroxybenzylamino | tetrahydropyran-2-yl | C = 59.5; H = 5.6; N = 20.9 | 340 | 342 |
| 18 | 3,4-dihydroxybenzylamino | tetrahydropyran-2-yl | C = 60.1; H = 5.7; N = 20.6 | 340 | 342 |
| 19 | 3,5-dihydroxybenzylamino | tetrahydropyran-2-yl | C = 60.1; H = 5.6; N = 20.7 | 340 | 342 |
| 20 | 4-hydroxy-3,5-dimethoxybenzylamino | tetrahydropyran-2-yl | C = 59.1; H = 5.8; N = 18.4 | 384 | 386 |
| 21 | 4-hydroxy-2,6-dimethoxybenzylamino | tetrahydropyran-2-yl | C = 59.1; H = 5.9; N = 18.6 | 384 | 386 |
| 22 | 4-hydroxy-3-methoxybenzylamino | tetrahydropyran-2-yl | C = 63.6; H = 6.3; N = 20.2 | 354 | 356 |
| 23 | 3-hydroxy-4-methoxybenzylamino | tetrahydropyran-2-yl | C = 63.5; H = 6.3; N = 20.2 | 354 | 356 |
| 24 | 2,3,4-trihydroxybenzylamino | tetrahydropyran-2-yl | C = 57.2; H = 5.4; N = 19.7 | 356 | 358 |
| 25 | 2,4,5-trihydroxybenzylamino | tetrahydropyran-2-yl | C = 57.2; H = 5.2; N = 20.2 | 356 | 358 |
| 26 | 2-hydroxy-3-methylbenzylamino | tetrahydropyran-2-yl | C = 63.4; H = 6.3; N = 20.2 | 338 | 340 |
| 27 | 2-hydroxy-5-methylbenzylamino | tetrahydropyran-2-yl | C = 63.1; H = 6.4; N = 20.4 | 338 | 340 |
| 28 | 4-hydroxy-3-methylbenzylamino | tetrahydropyran-2-yl | C = 63.5; H = 6.3; N = 20.5 | 338 | 340 |
| 29 | 4-hydroxy-5-methylbenzylamino | tetrahydropyran-2-yl | C = 63.7; H = 6.4; N = 20.4 | 338 | 340 |
| 30 | 3-hydroxyfurfurylamino | tetrahydropyran-2-yl | C = 57.0; H = 5.3; N = 22.4 | 314 | 316 |
| 31 | 4-hydroxyfurfurylamino | tetrahydropyran-2-yl | C = 57.0; H = 5.4; N = 22.3 | 314 | 316 |
| 32 | 5-hydroxyfurfurylamino | tetrahydropyran-2-yl | C = 57.1; H = 5.4; N = 22.3 | 314 | 316 |
| 33 | 5-hydroxy-pent-2-en-1-yl | tetrahydropyran-2-yl | C = 59.4; H = 6.9; N = 23.1 | 302 | 304 |
| 34 | 2-hydroxyanilino | tetrahydropyran-2-yl | C = 61.6; H = 5.6; N = 22.8 | 310 | 312 |
| 35 | 3-hydroxyanilino | tetrahydropyran-2-yl | C = 61.6; H = 5.5; N = 23.0 | 310 | 312 |
| 36 | 4-hydroxyanilino | tetrahydropyran-2-yl | C = 61.2; H = 5.5; N = 22.6 | 310 | 312 |

TABLE 1-continued

Compounds prepared by the method of examples 1-7

| | PURINE SUBSTITUENT | | CHN ANALYSES | MS ANALYSES-ZMD | |
|---|---|---|---|---|---|
| | R6 | R9 | [%] | $[M-H]^-$ a) | $[M+H]^+$ b) |
| 37 | 4-hydroxy-3-methylanilino | tetrahydropyran-2-yl | C = 62.7; H = 5.9; N = 21.7 | 324 | 326 |
| 38 | 4-hydroxy-5-methylanilino | tetrahydropyran-2-yl | C = 62.8; H = 5.9; N = 21.7 | 324 | 326 |
| 39 | 2,4-dihydroxyanilino | tetrahydropyran-2-yl | C = 58.6; H = 5.2; N = 21.7 | 326 | 328 |
| 40 | 3,4-dihydroxyanilino | tetrahydropyran-2-yl | C = 58.5; H = 5.2; N = 21.1 | 326 | 328 |
| 41 | 4-hydroxy-3,5-dimethoxyanilino | tetrahydropyran-2-yl | C = 58.0; H = 5.8; N = 19.1 | 370 | 372 |
| 42 | 4-hydroxy-2,6-dimethoxyanilino | tetrahydropyran-2-yl | C = 57.7; H = 5.8; N = 19.1 | 370 | 372 |
| 43 | 3-hydroxy-4-methoxyanilino | tetrahydropyran-2-yl | C = 59.6; H = 5.6; N = 20.8 | 340 | 342 |
| 44 | 2,3,4-trihydroxyanilino | tetrahydropyran-2-yl | C = 55.7; H = 5.1; N = 20.9 | 342 | 344 |
| 45 | 2,3,4-trihydroxyanilino | tetrahydropyran-2-yl | C = 59.8; H = 5.6; N = 20.5 | 340 | 342 |
| 46 | 1-methyl-4-hydroxy-3-methylbutylamino | tetrahydropyran-2-yl | C = 60.2; H = 7.9; N = 21.9 | 318 | 320 | a) solution: MeOH p.a. + HCOOH
b) solution: MeOH p.a. + $H_2O$ + $NH_3$

Example 8

6-(4-hydroxybenzylamino)-9-(tetrahydrofuran-2-yl)-purine. A mixture of 10 mmol (2240 mg) of 6-chloro-9-(tetrahydrofuran-2-yl)purine (prepared from 10 mmol (1546 mg) of 6-chloropurine), 12 mmol (1478 mg) of 4-hydroxybenzylamine, and 5 ml of N-ethyldiisopropylamine was refluxed in n-propanol for 3 hours. After removal of the n-propanol by vacuum evaporation, the resulting material was treated with water and extracted into ethyl acetate. The ethyl acetate phase was evaporated and the residuum subsequently washed with 30 ml of petroleum ether. The solid residue was filtered off and the crude product crystallized from methanol. Yield 80%, white solid. TLC (EtOAc:hexane (1:1) (v:v)): single spot; HPLC: purity >98%. $^1$H NMR (400 MHZ, DMSO): 1.36tt (2H, $J_a$=7.8 Hz, $J_b$=2.2 Hz); 2.23m (1H); 2.32m (1H); 3.62dd (1H, $J_a$=10.8 Hz, $J_b$=3.8 Hz); 3.87dd (1H, $J_a$=10.8 Hz, $J_b$=3.8 Hz); 4.62s (2H); 6.23dd (1H, $J_a$=5.3 Hz, $J_b$=1.5 Hz); 6.71d (2H, J=8.3 Hz); 7.21d (2H, J=8.3 Hz); 8.06bs (1); 8.16s (1H); 8.28s (1H); 9.23s (1H). MS (ES): $[M+H]^+$=312 (100).

Example 9

6-(3-hydroxybenzylamino)-9-(tetrahydrofuran-2-yl)-purine. A mixture of 10 mmol (2240 mg) of 6-chloro-9-(tetrahydrofuran-2-yl)-purine (prepared from 10 mmol (1546 mg) of 6-chloropurine), 12 mmol (1478 mg) of 3-hydroxybenzylamine, and 5 ml of N-ethyldiisopropylamine was refluxed in n-propanol for 3 hours. After removal of the n-propanol by vacuum evaporation, the resulting material was treated with water and extracted into ethyl acetate. The ethyl acetate phase was evaporated and the residuum subsequently washed with 30 ml of petroleum ether. The solid residue was filtered off and the crude product crystallized from methanol. Yield 85%, white solid. TLC (EtOAc:hexane (1:1) (v:v)): single spot; HPLC: purity >98%. $^1$H NMR (400 MHZ, DMSO): 2.20sep (1H, J=6.8 Hz); 2.22sep (1H, J=6.8 Hz); 2.44m (2H); 3.91q (1H, J=7.3 Hz); 4.14q (1H, J=7.3 Hz); 4.63bs (2H); 6.26m (1H); 6.59dd (1H, $J_a$=7.8 Hz, $J_b$=2.2 Hz); 6.73s (1H); 6.75d (1H, J=7.8 Hz); 7.07t (1H, J=7.8 Hz); 8.20s (1H); 8.26bs (1H); 8.27s (1H); 9.23bs (1H). MS (ES): $[M+H]^+$=312 (100).

Example 10

6-(2-hydroxybenzylamino)-9-(tetrahydrofuran-2-yl)-purine. A mixture of 10 mmol (2240 mg) of 6-chloro-9-(tetrahydrofuran-2-yl)-purine (prepared from 10 mmol (1546 mg) of 6-chloropurine), 12 mmol (1478 mg) of 2-hydroxybenzylamine, and 5 ml of triethylamine was refluxed in n-propanol for 3 hours. After removal of the n-propanol by vacuum evaporation, the resulting material was treated with water and extracted into ethyl acetate. The ethyl acetate phase was evaporated and the residuum subsequently washed with 30 ml of petroleum ether. The solid residue was filtered off and the crude product crystallized from methanol. Yield 80%, white solid. TLC (EtOAc:hexane) (1:1) (v:v): single spot; HPLC: purity >98%. $^1$H NMR (400 MHZ, DMSO): 2.22sep (1H); 2.44m (1H); 3.82q (1H, J=7.3 Hz); 4.15q (1H, J=7.3 Hz); 4.69bs (2H); 6.26m (1H); 6.73t (1H, J=7.5 Hz); 6.82d (1H, J=7.9 Hz); 7.06t (1H, J=7.8 Hz); 7.17d (1H, J=7.3 Hz); 8.05bs (1H); 8.22s (1H); 8.23s (1H); 9.82bs (1H). MS (ES): $[M+H]^+$=312 (100).

Example 11

6-(4-hydroxy-3-methoxybenzylamino)-9-(tetrahydrofuran-2-yl)-purine. A mixture of 10 mmol (2240 mg) of 6-chloro-9-(tetrahydrofuran-2-yl)-purine (prepared from 10 mmol (1546 mg) of 6-chloropurine), 12 mmol (1838 mg) of 4-hydroxy-3-methoxybenzylamine and 5 mL of triethylamine was refluxed in n-propanol for 3 hours. After removal of the n-propanol by vacuum evaporation, the resulting material was treated with water and extracted into ethyl acetate. The ethyl acetate phase was evaporated and the residuum subsequently washed with 30 ml of petroleum ether. The solid residue was filtered off and the crude product crystallized from methanol. Yield 80%, white solid. TLC (EtOAc:hexane) (1:1) (v:v): single spot; HPLC: purity >98%. $^1$H NMR (400 MHZ, DMSO): 0.90d (3H, J=6.6 Hz); 1.32m (1H); 1.57m (1H); 1.84m (1H); 1.95m (1H); 2.12m (2H); 2.29m (1H); 3.26m (1H); 3.51bs (2H); 3.73m (1H); 3.89m (1H); 4.40t (1H, J=5.1 Hz); 6.12d (1H, J=5.2 Hz); 7.74bs (1H); 8.18s (1H); 8.28s (1H. MS (ES): $[M+H]^+$=342 (100).

TABLE 2

Compounds prepared by the method of example 8-11

| | PURINE SUBSTITUENT | | CHN ANALYSES | MS ANALYSES-ZMD | |
|---|---|---|---|---|---|
| | R6 | R9 | [%] | [M − H]$^-$ a) | [M + H]$^+$ b) |
| 47 | (E)-(4-hydroxy-2-methylbut-2-en-1-ylamino) | tetrahydrofuran-2-yl | C = 57.7; H = 6.3; N = 24.7 | 288 | 290 |
| 47 | (Z)-(4-hydroxy-3-methylbut-2-en-1-ylamino) | tetrahydrofuran-2-yl | C = 58.6; H = 6.8; N = 23.9 | 288 | 290 |
| 49 | (E)-(4-hydroxy-3-methylbut-2-en-1-ylamino) | tetrahydrofuran-2-yl | C = 57.9; H = 6.4; N = 24.5 | 288 | 290 |
| 50 | (Z)-(4-hydroxy-1,3-dimethylbut-2-en-1-ylamino) | tetrahydrofuran-2-yl | C = 59.0; H = 7.2; N = 23.1 | 302 | 304 |
| 51 | (E)-(4-hydroxy-1,3-dimethylbut-2-en-1-ylamino) | tetrahydrofuran-2-yl | C = 59.0; H = 7.2; N = 23.3 | 302 | 304 |
| 52 | 4-hydroxy-3-methylbutylamino | tetrahydrofuran-2-yl | C = 57.8; H = 7.3; N = 24.1 | 290 | 292 |
| 53 | 1-methyl-4-hydroxy-3-methylbutylamino | tetrahydrofuran-2-yl | C = 59.0; H = 7.6; N = 22.9 | 304 | 306 |
| 54 | 4-hydroxybut-2-en-1-ylamino | tetrahydrofuran-2-yl | C = 56.7; H = 6.2; N = 25.4 | 274 | 276 |
| 55 | 2-hydroxybenzylamino | tetrahydrofuran-2-yl | C = 61.5; H = 5.5; N = 22.7 | 310 | 312 |
| 56 | 3-hydroxybenzylamino | tetrahydrofuran-2-yl | C = 61.5; H = 5.4; N = 22.5 | 310 | 312 |
| 57 | 4-hydroxybenzylamino | tetrahydrofuran-2-yl | C = 61.5; H = 5.4; N = 22.7 | 310 | 312 |
| 58 | 2-hydroxy-3-methoxybenzylamino | tetrahydrofuran-2-yl | C = 59.7; H = 5.1; N = 21.0 | 340 | 342 |
| 59 | 2-hydroxy-4-methoxybenzylamino | tetrahydrofuran-2-yl | C = 59.5; H = 5.5; N = 20.9 | 340 | 342 |
| 60 | 2-hydroxy-5-methoxybenzylamino | tetrahydrofuran-2-yl | C = 59.6; H = 5.5; N = 20.7 | 340 | 342 |
| 61 | 2,3-dihydroxybenzylamino | tetrahydrofuran-2-yl | C = 58.5; H = 5.2; N = 21.5 | 326 | 328 |
| 62 | 2,4-dihydroxybenzylamino | tetrahydrofuran-2-yl | C = 58.7; H = 5.1; N = 21.5 | 326 | 328 |
| 63 | 2,5-dihydroxybenzylamino | tetrahydrofuran-2-yl | C = 58.8; H = 5.1; N = 21.4 | 326 | 328 |
| 64 | 2,6-dihydroxybenzylamino | tetrahydrofuran-2-yl | C = 58.5; H = 5.1; N = 21.7 | 326 | 328 |
| 65 | 3,4-dihydroxybenzylamino | tetrahydrofuran-2-yl | C = 58.7; H = 5.2; N = 21.5 | 326 | 328 |
| 66 | 3,5-dihydroxybenzylamino | tetrahydrofuran-2-yl | C = 58.5; H = 5.1; N = 21.5 | 326 | 328 |
| 67 | 4-hydroxy-3,5-dimethoxybenzylamino | tetrahydrofuran-2-yl | C = 58.0; H = 5.6; N = 19.3 | 370 | 372 |
| 68 | 4-hydroxy-2,6-dimethoxybenzylamino | tetrahydrofuran-2-yl | C = 57.7; H = 5.6; N = 19.5 | 370 | 372 |
| 69 | 4-hydroxy-3-methoxybenzylamino | tetrahydrofuran-2-yl | C = 59.7; H = 5.5; N = 20.8 | 340 | 342 |
| 70 | 3-hydroxy-4-methoxybenzylamino | tetrahydrofuran-2-yl | C = 59.8; H = 5.6; N = 20.6 | 340 | 342 |
| 71 | 2,3,4-trihydroxybenzylamino | tetrahydrofuran-2-yl | C = 59.7; H = 6.0; N = 18.3 | 384 | 386 |
| 72 | 2,4,5-trihydroxybenzylamino | tetrahydrofuran-2-yl | C = 59.2; H = 6.1; N = 18.7 | 384 | 386 |
| 73 | 2-hydroxy-3-methylbenzylamino | tetrahydrofuran-2-yl | C = 62.5; H = 6.0; N = 22.0 | 324 | 326 |
| 74 | 2-hydroxy-5-methylbenzylamino | tetrahydrofuran-2-yl | C = 62.1; H = 5.8; N = 21.9 | 324 | 326 |
| 75 | 4-hydroxy-3-methylbenzylamino | tetrahydrofuran-2-yl | C = 62.9; H = 5.8; N = 21.4 | 324 | 326 |
| 76 | 4-hydroxy-5-methylbenzylamino | tetrahydrofuran-2-yl | C = 62.6; H = 5.8; N = 21.6 | 324 | 326 |
| 77 | 3-hydroxyfurfurylamino | tetrahydrofuran-2-yl | C = 55.5; H = 5.1; N = 23.8 | 300 | 302 |
| 78 | 4-hydroxyfurfurylamino | tetrahydrofuran-2-yl | C = 55.9; H = 5.2; N = 22.7 | 300 | 302 |
| 79 | 5-hydroxyfurfurylamino | tetrahydrofuran-2-yl | C = 55.4; H = 4.9; N = 23.5 | 300 | 302 |
| 80 | 5-hydroxy-pent-2-en-1-yl | tetrahydrofuran-2-yl | C = 58.1; H = 6.6; N = 24.2 | 288 | 290 |
| 81 | 2-hydroxyanilino | tetrahydrofuran-2-yl | C = 60.3; H = 5.0; N = 23.6 | 296 | 298 |
| 82 | 3-hydroxyanilino | tetrahydrofuran-2-yl | C = 60.1; H = 5.1; N = 23.7 | 296 | 298 |

TABLE 2-continued

Compounds prepared by the method of example 8-11

| | PURINE SUBSTITUENT | | CHN ANALYSES | MS ANALYSES-ZMD | |
|---|---|---|---|---|---|
| | R6 | R9 | [%] | [M − H]⁻ a) | [M + H]⁺ b) |
| 83 | 4-hydroxyanilino | tetrahydrofuran-2-yl | C = 60.4; H = 5.0; N = 23.7 | 296 | 298 |
| 84 | 4-hydroxy-3-methylanilino | tetrahydrofuran-2-yl | C = 61.5; H = 5.2; N = 22.7 | 310 | 312 |
| 85 | 4-hydroxy-5-methylanilino | tetrahydrofuran-2-yl | C = 61.6; H = 5.2; N = 22.8 | 310 | 312 |
| 86 | 2,4-dihydroxyanilino | tetrahydrofuran-2-yl | C = 57.1; H = 4.7; N = 22.7 | 312 | 314 |
| 87 | 3,4-dihydroxyanilino | tetrahydrofuran-2-yl | C = 57.4; H = 4.8; N = 22.3 | 312 | 314 |
| 88 | 4-hydroxy-3,5-dimethoxyanilino | tetrahydrofuran-2-yl | C = 56.9; H = 5.4; N = 20.1 | 356 | 358 |
| 89 | 4-hydroxy-2,6-dimethoxyanilino | tetrahydrofuran-2-yl | C = 57.0; H = 5.6; N = 19.9 | 356 | 358 |
| 90 | 3-hydroxy-4-methoxyanilino | tetrahydrofuran-2-yl | C = 58.4; H = 5.6; N = 21.5 | 326 | 328 |
| 91 | 4-hydroxy-3-methoxyanilino | tetrahydrofuran-2-yl | C = 58.7; H = 5.2; N = 21.4 | 326 | 328 |
| 92 | 2,3,4-trihydroxyanilino | tetrahydrofuran-2-yl | C = 54.1; H = 4.4; N = 19.9 | 328 | 330 |
| 93 | 2,4,5-trihydroxyanilino | tetrahydrofuran-2-yl | C = 54.3; H = 4.3; N = 19.8 | 328 | 330 | a) solution: MeOH p.a. + HCOOH
b) solution: MeOH p.a. + $H_2O$ + $NH_3$

Example 12

6-(4-hydroxybenzylamine)-9-(4-chlorobutyl)purine. A mixture of 10 mmol (2451 mg) of 6-chloro-9-(4-chlorobutyl)purine (prepared from 10 mmol (1546 mg) of 6-chloropurine), 12 mmol (1478 mg) of 4-hydroxybenzylamine and 5 mL of triethylamine was refluxed in n-butanol for 3 hrs. After removal of the n-butanol by vacuum evaporation, the resulting material was treated with water and extracted into ethyl acetate. The ethyl acetate solvent was evaporated and the residuum subsequently washed with 30 ml of diethylether. The solid residue was filtered off and crude product crystallized from methanol. Yield: 70%, white solid. TLC ($CHCl_3$: $CH_3OH$:$NH_3$) (85:15:0.1) (v:v): single spot; HPLC: purity >98%. $^1$H NMR (400 MHZ, DMSO): 1.89m (4H); 3.46dd (2H, $J_a$=11.0 Hz, $J_b$=3.6 Hz); 4.22tt (2H, $J_a$=13.0 Hz, $J_b$=3.5 Hz); 4.61s (2H); 6.59 d (2H, J=8.3 Hz); 7.27d (2H, J=8.3 Hz); 8.18s (1H); 8.22bs (1H); 8.31s (1H); 9.18s (1H). MS (ES): [M+H]⁺=346 (100).

TABLE 3

Compounds prepared by the method of example 12

| | PURINE SUBSTITUENT | | CHN ANALYSES | MS ANALYSES-ZMD | |
|---|---|---|---|---|---|
| | R6 | R9 | [%] | [M − H]⁻* a) | [M + H]⁺* b) |
| 94 | (Z)-(4-hydroxy-3-methylbut-2-en-1-ylamino) | 4-chlorobutyl | C = 54.2; H = 6.5; N = 22.7 | 308 | 310 |
| 95 | (E)-(4-hydroxy-3-methylbut-2-en-1-ylamino) | 4-chlorobutyl | C = 54.0; H = 6.4; N = 23.1 | 308 | 310 |
| 96 | 4-hydroxy-3-methylbutylamino | 4-chlorobutyl | C = 53.5; H = 7.1; N = 23.1 | 310 | 312 |
| 97 | 1-methyl-4-hydroxy-3-methylbutylamino | 4-chlorobutyl | C = 55.3; H = 7.4; N = 21.5 | 324 | 326 |
| 98 | 4-hydroxybut-2-en-1-ylamino | 4-chlorobutyl | C = 52.8; H = 6.1; N = 11.9 | 294 | 296 |
| 99 | 2-hydroxybenzylamino | 4-chlorobutyl | C = 57.5; H = 5.5; N = 21.2 | 344 | 346 |
| 100 | 3-hydroxybenzylamino | 4-chlorobutyl | C = 58.1; H = 5.5; N = 21.3 | 344 | 346 |
| 101 | 4-hydroxybenzylamino | 4-chlorobutyl | C = 57.8; H = 5.4; N = 21.7 | 344 | 346 |
| 102 | 2-hydroxy-3-methoxybenzylamino | 4-chlorobutyl | C = 55.9; H = 5.5; N = 19.9 | 360 | 362 |
| 103 | 2-hydroxy-4-methoxybenzylamino | 4-chlorobutyl | C = 56.1; H = 5.6; N = 19.7 | 360 | 362 |
| 104 | 2-hydroxy-5-methoxybenzylamino | 4-chlorobutyl | C = 56.5; H = 5.7; N = 19.0 | 360 | 362 |
| 105 | 2,3-dihydroxybenzylamino | 4-chlorobutyl | C = 55.2; H = 5.1; N = 20.4 | 346 | 348 |

TABLE 3-continued

Compounds prepared by the method of example 12

| | PURINE SUBSTITUENT | | CHN ANALYSES | MS ANALYSES-ZMD | |
|---|---|---|---|---|---|
| | R6 | R9 | [%] | $[M-H]^{-*}$ a) | $[M+H]^{+*}$ b) |
| 106 | 2,4-dihydroxybenzylamino | 4-chlorobutyl | C = 55.1; H = 5.2; N = 20.6 | 346 | 348 |
| 107 | 2,5-dihydroxybenzylamino | 4-chlorobutyl | C = 55.2; H = 5.2; N = 20.4 | 346 | 348 |
| 108 | 2,6-dihydroxybenzylamino | 4-chlorobutyl | C = 55.1; H = 5.1; N = 20.4 | 346 | 348 |
| 109 | 3,4-dihydroxybenzylamino | 4-chlorobutyl | C = 55.0; H = 5.2; N = 20.1 | 346 | 348 |
| 110 | 3,5-dihydroxybenzylamino | 4-chlorobutyl | C = 55.3; H = 5.2; N = 20.2 | 346 | 348 |
| 111 | 4-hydroxy-3,5-dimethoxybenzylamino | 4-chlorobutyl | C = 55.0; H = 5.7; N = 18.1 | 390 | 392 |
| 112 | 4-hydroxy-2,6-dimethoxybenzylamino | 4-chlorobutyl | C = 55.1; H = 5.7; N = 18.2 | 390 | 392 |
| 113 | 4-hydroxy-3-methoxybenzylamino | 4-chlorobutyl | C = 56.1; H = 5.6; N = 19.6 | 360 | 362 |
| 114 | 3-hydroxy-4-methoxybenzylamino | 4-chlorobutyl | C = 56.1; H = 5.5; N = 19.7 | 360 | 362 |
| 115 | 2,3,4-trihydroxybenzylamino | 4-chlorobutyl | C = 52.1; H = 4.7; N = 19.8 | 362 | 364 |
| 116 | 2,4,5-trihydroxybenzylamino | 4-chlorobutyl | C = 52.4; H = 4.9; N = 19.5 | 362 | 364 |
| 117 | 2-hydroxy-3-methylbenzylamino | 4-chlorobutyl | C = 58.7; H = 5.7; N = 20.7 | 344 | 346 |
| 118 | 2-hydroxy-5-methylbenzylamino | 4-chlorobutyl | C = 59.2; H = 5.9; N = 19.9 | 344 | 346 |
| 119 | 4-hydroxy-3-methylbenzylamino | 4-chlorobutyl | C = 58.7; H = 5.8; N = 20.4 | 344 | 346 |
| 120 | 4-hydroxy-5-methylbenzylamino | 4-chlorobutyl | C = 58.9; H = 5.7; N = 20.4 | 344 | 346 |
| 121 | 3-hydroxyfurfurylamino | 4-chlorobutyl | C = 52.2; H = 5.0; N = 22.4 | 320 | 322 |
| 122 | 4-hydroxyfurfurylamino | 4-chlorobutyl | C = 52.1; H = 5.0; N = 22.1 | 320 | 322 |
| 123 | 5-hydroxyfurfurylamino | 4-chlorobutyl | C = 52.4; H = 5.2; N = 21.9 | 320 | 322 |
| 124 | 2-hydroxyanilino | 4-chlorobutyl | C = 56.7; H = 5.1; N = 21.9 | 316 | 318 |
| 125 | 3-hydroxyanilino | 4-chlorobutyl | C = 56.3; H = 5.0; N = 22.3 | 316 | 318 |
| 126 | 4-hydroxyanilino | 4-chlorobutyl | C = 56.6; H = 5.0; N = 22.4 | 316 | 318 | a) solution: MeOH p.a. + HCOOH
b) solution: MeOH p.a. + $H_2O$ + $NH_3$
*for $Cl^{35}$

Example 13

6-(4-hydroxybenzylamine)-9-(1-ethoxyeth-2-yl)purine. A mixture of 10 mmol (2270 mg) of 6-chloro-9-(1-ethoxyeth-2-yl)purine made of 10 mmol (1546 mg) of 6-chloropurine, 12 mmol (1478 mg) of 4-hydroxybenzylamine, and 4 mL of N-ethyldiisopropylamine was refluxed in n-butanol for 3 hrs. After removal of the n-butanol by vacuum evaporation, the resulting material was treated with water and extracted into ethyl acetate. The ethyl acetate phase was evaporated and the residuum subsequently washed with 30 ml of hexane. The solid residue was filtered off and the crude product crystallized from isopropanol. Yield: 65%, white solid. TLC ($CHCl_3$:$CH_3OH$:$NH_3$ (85:15:0.1) (v:v): single spot; HPLC: purity >98%. $^1$H NMR (400 MHZ, DMSO): 1.12t (3H, J=6.8 Hz); 3.16m (1H); 3.23m (1H); 3.82dd (2H, $J_a$=13.0 Hz, $J_b$=3.8 Hz); 4.31m (2H); 4.60s (2H); 6.70d (2H, J=8.3 Hz); 7.30d (2H, J=8.3 Hz); 8.18bs (1H); 8.23s (1H); 8.32s (1H); 9.25s (1H). MS (ES): $[M+H]^+$=314 (100).

TABLE 4

Compounds prepared by the method of example 13

| | PURINE SUBSTITUENT | | CHN ANALYSES | MS ANALYSES-ZMD | |
|---|---|---|---|---|---|
| | R6 | R9 | [%] | $[M-H]^{-*}$ a) | $[M+H]^{+*}$ b) |
| 127 | (Z)-(4-hydroxy-3-methylbut-2-en-1-ylamino) | 1-ethoxyeth-2-yl | C = 57.0; H = 7.2; N = 24.3 | 290 | 292 |

TABLE 4-continued

Compounds prepared by the method of example 13

| | PURINE SUBSTITUENT | | CHN ANALYSES | MS ANALYSES-ZMD | |
|---|---|---|---|---|---|
| | R6 | R9 | [%] | $[M - H]^{-*}$ a) | $[M + H]^{+*}$ b) |
| 128 | (E)-(4-hydroxy-3-methylbut-2-en-1-ylamino) | 1-ethoxyeth-2-yl | C = 57.1; H = 7.3; N = 24.2 | 290 | 292 |
| 129 | 4-hydroxy-3-methylbutylamino | 1-ethoxyeth-2-yl | C = 57.1; H = 7.6; N = 24.2 | 292 | 294 |
| 130 | 4-hydroxybut-2-en-1-ylamino | 1-ethoxyeth-2-yl | C = 56.3; H = 6.9; N = 25.2 | 276 | 278 |
| 131 | 2-hydroxybenzylamino | 1-ethoxyeth-2-yl | C = 60.9; H = 6.0; N = 22.9 | 312 | 314 |
| 132 | 3-hydroxybenzylamino | 1-ethoxyeth-2-yl | C = 61.1; H = 6.0; N = 22.5 | 312 | 314 |
| 133 | 4-hydroxybenzylamino | 1-ethoxyeth-2-yl | C = 60.8; H = 6.1; N = 22.5 | 312 | 314 |
| 134 | 2-hydroxy-3-methoxybenzylamino | 1-ethoxyeth-2-yl | C = 59.1; H = 6.0; N = 21.0 | 342 | 344 |
| 135 | 2-hydroxy-4-methoxybenzylamino | 1-ethoxyeth-2-yl | C = 59.5; H = 6.0; N = 20.6 | 342 | 344 |
| 136 | 2-hydroxy-5-methoxybenzylamino | 1-ethoxyeth-2-yl | C = 59.3; H = 6.0; N = 20.9 | 342 | 344 |
| 137 | 2,3-dihydroxybenzylamino | 1-ethoxyeth-2-yl | C = 58.0; H = 5.7; N = 21.4 | 328 | 330 |
| 138 | 2,4-dihydroxybenzylamino | 1-ethoxyeth-2-yl | C = 58.5; H = 5.5; N = 21.9 | 328 | 330 |
| 139 | 2,5-dihydroxybenzylamino | 1-ethoxyeth-2-yl | C = 58.4; H = 5.8; N = 21.3 | 328 | 330 |
| 140 | 2,6-dihydroxybenzylamino | 1-ethoxyeth-2-yl | C = 58.5; H = 5.8; N = 21.7 | 328 | 330 |
| 141 | 3,4-dihydroxybenzylamino | 1-ethoxyeth-2-yl | C = 58.1; H = 5.7; N = 21.7 | 328 | 330 |
| 142 | 3,5-dihydroxybenzylamino | 1-ethoxyeth-2-yl | C = 58.3; H = 5.8; N = 21.8 | 328 | 330 |
| 143 | 4-hydroxy-3,5-dimethoxybenzylamino | 1-ethoxyeth-2-yl | C = 57.4; H = 6.4; N = 19.0 | 372 | 374 |
| 144 | 4-hydroxy-2,6-dimethoxybenzylamino | 1-ethoxyeth-2-yl | C = 57.6; H = 6.8; N = 19.3 | 372 | 374 |
| 145 | 4-hydroxy-3-methoxybenzylamino | 1-ethoxyeth-2-yl | C = 59.2; H = 6.2; N = 20.4 | 342 | 344 |
| 146 | 3-hydroxy-4-methoxybenzylamino | 1-ethoxyeth-2-yl | C = 59.0; H = 6.3; N = 20.4 | 342 | 344 |
| 147 | 2,3,4-trihydroxybenzylamino | 1-ethoxyeth-2-yl | C = 55.5; H = 5.6; N = 20.8 | 344 | 346 |
| 148 | 2,4,5-trihydroxybenzylamino | 1-ethoxyeth-2-yl | C = 55.1; H = 5.3; N = 20.4 | 344 | 346 | a) solution: MeOH p.a. + HCOOH
b) solution: MeOH p.a. + $H_2O$ + $NH_3$
*for $Cl^{35}$

Example 14

Estimation of cytokinin biological activity of novel compounds in callus bioassay. Cytokinin-dependent tobacco callus *Nicotiana tabacum* L. cv. Wisconsin 38 was maintained at 25° C. in darkness on modified MS medium, containing per 1 liter: 4 mmol of nicotinic acid, 2.4 mmol of pyridoxine hydrochloride, 1.2 mmol of thiamine, 26.6 mmol of glycine, 1.37 mmol of glutamine, 1.8 mmol of myo-inositol, 30 g of sucrose, 8 g of agar, 5.37 mmol of NAA, and 0.5 mmol of the compound tested. Subcultivation was carried out every three weeks. Fourteen days before the bioassay, the callus tissue was transferred to the media without the compound tested. The biological activity was determined from the increase of the fresh callus weight after four weeks of cultivation. Five replicates were prepared for each concentration of the compound tested and the entire test was repeated twice. From the obtained data, the concentration with the highest activity was selected for each compound tested. The relative activity of the compound at this concentration was calculated (Table 8). The activity obtained for $10^{-5}$ M 6-benzylaminopurine (BAP) was defined as 100%.

The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used.

The compounds listed in Table 5 can be divided into two groups. The first group contains natural cytokinins represented by $N^6$-substituted purines (compounds known in the prior art serving as control). The second group contains the novel 6,9-disubstituted purines derived from the compounds of the first group. The results in Table 5 show that the substitution in position 9 of the purine ring by tetrahydropyranyl, tetrahydrofuranyl and other easily cleavable substituents generally led to an increase of the cytokinin activity in the callus bioassay in comparison to the original cytokinin analogues.

TABLE 5

The effect of novel compounds on the growth of cytokinin-dependent
tobacco callus *Nicotiana tabacum* L. cv. Wisconsin 38

| Tested compound | | concentration with highest activity | activity (%) |
|---|---|---|---|
| R6 | R9 | $(mol \cdot l^{-1})$ | $[10^{-5} mol \cdot l^{-1} BAP = 100\%]$ |
| benzylamino | H | $10^{-6}$ | 100 |
| benzylamino | tetrahydropyran-2-yl | $10^{-6}$ | 103 (±12) |
| 2-hydroxybenzylamino | H | $10^{-5}$ | 72.3 (±9) |
| 2-hydroxybenzylamino | tetrahydropyran-2-yl | $10^{-5}$ | 80 (±7) |
| 2-hydroxybenzylamino | tetrahydrofuran-2-yl | $10^{-5}$ | 78 (±8) |
| 3-hydroxybenzylamino | H | $10^{-5}$ | 116 (±11) |
| 3-hydroxybenzylamino | tetrahydropyran-2-yl | $10^{-5}$ | 139 (±16) |
| 3-hydroxybenzylamino | tetrahydrofuran-2-yl | $10^{-5}$ | 125 (±14) |
| 3-hydroxybenzylamino | 4-chlorobutyl | $10^{-4}$ | 111.6 (±20) |
| 3-hydroxybenzylamino | 1-ethoxyethyl | $10^{-4}$ | 109.4 (±14) |
| 4-hydroxybenzylamino | H | | n.a. |
| 4-hydroxybenzylamino | tetrahydropyran-2-yl | $10^{-5}$ | 36 (±5) |
| 4-hydroxybenzylamino | tetrahydrofuran-2-yl | $10^{-5}$ | 27 (±6) |
| (E)-(4-hydroxy-3-methylbut-2-en-1-ylamino) | H | $10^{-5}$ | 86.9 (±12) |
| (E)-(4-hydroxy-3-methylbut-2-en-1-ylamino) | tetrahydropyran-2-yl | $10^{-5}$ | 96.5 (±3) |
| (E)-(4-hydroxy-3-methylbut-2-en-1-ylamino) | tetrahydrofuran-2-yl | $10^{-5}$ | 89 (±12) |
| (E)-(4-hydroxy-3-methylbut-2-en-1-ylamino) | 4-chlorobutyl | $10^{-4}$ | 103.5 (±16) |
| (E)-(4-hydroxy-3-methylbut-2-en-1-ylamino) | 1-ethoxyethyl | $10^{-4}$ | 102.8 (±15) |
| 4-hydroxy-3-methylbutylamino | H | $10^{-5}$ | 83.2 (±15) |
| 4-hydroxy-3-methylbutylamino | tetrahydropyran-2-yl | $10^{-5}$ | 112 (±13) |
| 4-hydroxy-3-methylbutylamino | tetrahydrofuran-2-yl | $10^{-5}$ | 105 (±11) |
| 4-hydroxy-3-methylbutylamino | 4-chlorobutyl | $10^{-4}$ | 84 (±8) |
| 4-hydroxy-3-methylbutylamino | 1-ethoxyethyl | $10^{-4}$ | 95 (±6) |
| 2-hydroxy-3-methoxybenzylamino* | H | | n.a. |
| 2-hydroxy-3-methoxybenzylamino | tetrahydropyran-2-yl | $10^{-6}$ | 11 (±1) |
| 3,5-dihydroxybenzylamino* | H | $10^{-6}$ | 39 (±6) |
| 3,5-dihydroxybenzylamino | tetrahydropyran-2-yl | $10^{-6}$ | 45 (±4) |
| 2-hydroxy-4-methoxybenzylamino | tetrahydropyran-2-yl | $10^{-6}$ | 43 (±2) |
| 2,4-dihydroxybenzylamino | tetrahydropyran-2-yl | $10^{-5}$ | 5 (±4) |
| 2,5-dihydroxybenzylamino | tetrahydropyran-2-yl | $10^{-5}$ | 20 (±8) |
| 3,4-dihydroxybenzylamino | tetrahydropyran-2-yl | $10^{-5}$ | 61 (±13) |
| 4-hydroxy-3,5-dimethoxybenzylamino | tetrahydropyran-2-yl | $10^{-5}$ | 39 (±12) |
| 4-hydroxy-2,6-dimethoxybenzylamino | tetrahydropyran-2-yl | $10^{-5}$ | 43 (±15) |
| 4-hydroxy-3-methoxybenzylamino | tetrahydropyran-2-yl | $10^{-6}$ | 62 (±6) |
| 3-hydroxy-4-methoxybenzylamino | tetrahydropyran-2-yl | $10^{-6}$ | 55 (±17) |
| 2-hydroxy-3-methylbenzylamino | tetrahydropyran-2-yl | $10^{-5}$ | 9.2 (±7) |
| 2-hydroxy-5-methylbenzylamino | tetrahydropyran-2-yl | $10^{-4}$ | 121 (±11) |
| 4-hydroxy-3-methylbenzylamino | tetrahydropyran-2-yl | $10^{-5}$ | 4 (±3) |
| 4-hydroxy-5-methylbenzylamino | tetrahydropyran-2-yl | $10^{-5}$ | 6 (±2) |
| 3-hydroxyfurfurylamino | tetrahydropyran-2-yl | $10^{-6}$ | 52 (±17) |
| 4-hydroxyfurfurylamino | tetrahydropyran-2-yl | $10^{-6}$ | 91 (±13) |
| 2-hydroxyanilino | tetrahydropyran-2-yl | $10^{-5}$ | 30 (±9) |
| 3-hydroxyanilino | tetrahydropyran-2-yl | $10^{-5}$ | 65 (±13) |
| 4-hydroxyanilino | tetrahydropyran-2-yl | $10^{-5}$ | 22 (±6) |
| 4-hydroxy-3-methylanilino | tetrahydropyran-2-yl | $10^{-5}$ | 12 (±4) |
| 4-hydroxy-5-methylanilino | tetrahydropyran-2-yl | $10^{-5}$ | 10 (±7) |
| 4-hydroxy-3,5-dimethoxyanilino | tetrahydropyran-2-yl | $10^{-5}$ | 19 (±9) |
| 4-hydroxy-2,6-dimethoxyanilino | tetrahydropyran-2-yl | $10^{-5}$ | 15 (±11) |

TABLE 5-continued

The effect of novel compounds on the growth of cytokinin-dependent
tobacco callus *Nicotiana tabacum* L. cv. Wisconsin 38

| Tested compound | | concentration with highest activity | activity (%) |
|---|---|---|---|
| R6 | R9 | $(mol \cdot l^{-1})$ | $[10^{-5} mol \cdot l^{-1} BAP = 100\%]$ |
| 4-hydroxy-3,5-dimethoxybenzylamino | tetrahydrofuran-2-yl | $10^{-5}$ | 27 (±9) |
| 4-hydroxy-2,6-dimethoxybenzylamino | tetrahydrofuran-2-yl | $10^{-5}$ | 31 (±7) |
| 3-hydroxy-4-methoxybenzylamino | tetrahydrofuran-2-yl | $10^{-6}$ | 47 (±12) |
| 4-hydroxy-3-methylbenzylamino | tetrahydrofuran-2-yl | $10^{-5}$ | 12 (±3) |
| 4-hydroxy-5-methylbenzylamino | tetrahydrofuran-2-yl | $10^{-5}$ | 2 (±0.8) |
| 4-hydroxyanilino | tetrahydrofuran-2-yl | $10^{-5}$ | 10 (±3) |
| 4-hydroxy-3-methylanilino | tetrahydrofuran-2-yl | $10^{-5}$ | 7 (±2) | n.a. means not active
*the control cytokinins described in Doležal et al. (Bioorg. Med.Chem. 14: 875, 2006).

Example 15

Testing of novel compounds for typical cytokinin activity in *Amaranthus* bioassay. A standard *Amaranthus* bioassay was performed with several modifications. The seeds of *Amaranthus caudatus* var. *atropurpurea* were surface-sterilized in 10% (w/v) N-chlorobenzenesulfonamide for 10 min and washed 5 times with deionized water. They were placed in 14 cm Petri dishes containing paper tissues saturated with deionized water. After 72 h of cultivation at 25° C. in darkness, the roots of the seedlings were cut off. The explants, consisting of two cotyledons and hypocotyls, were placed in 5 cm Petri dishes onto two layers of filter paper soaked with 1 ml of the incubation medium containing 10 mmol of $NA_2HPO_4$—$KH_2PO_4$, pH 6.8, 5 mmol of tyrosine and the compound to be tested. There were 20 explants per dish. The procedure was carried out under a green safe light in a darkroom. After 48 h of incubation at 25° C. in darkness, betacyanin was extracted by freezing the explants in 4 ml 3.33 mM acetic acid. The concentration of betacyanin was determined from the absorbencies at 537 nm and 620 nm as follows: $DA=A_{537\ nm}-A_{620\ nm}$. From the obtained data, the concentration with the highest activity was selected for each compound tested. Relative activity of the compound at this concentration was calculated. The activity obtained for $10^{-5}$ M 6-benzylaminopurine (BAP) was defined as 100%. The values shown in Table 6 are means of five replicates and the entire test was repeated twice.

The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used.

The compounds listed in Table 6 can be again divided into two groups. The first group contains classical cytokinins represented by $N^6$-substituted purines (compounds known in the prior art serving as control). The second group contains the novel 6,9-disubstituted derivatives of the compounds of the first group. The results show that the substitution in position 9 of the purine skeleton generally led to an increase of betacyanin (purple color) content in *Amaranthus caudatus* cotyledon/hypocotyl explants in comparison to the corresponding natural cytokinins.

TABLE 6

The effect of novel compounds on the betacyanin content in
*Amaranthus caudatus* cotyledon/hypocotyl explants

| Tested compound | | Concentration with highest activity | Activity (%) |
|---|---|---|---|
| R6 | R9 | $(mol \cdot l^{-1})$ | $[10^{-5} mol \cdot l^{-1} BAP = 100\%]$ |
| benzylamino | H | $10^{-5}$ | 100 |
| benzylamino | tetrahydropyran-2-yl | $10^{-4}$ | 120.7 (±18) |
| 2-hydroxybenzylamino | H | $10^{-4}$ | 32.6 (±12) |
| 2-hydroxybenzylamino | tetrahydropyran-2-yl | $10^{-4}$ | 41.6 (±5) |
| 2-hydroxybenzylamino | tetrahydrofuran-2-yl | $10^{-4}$ | 33 (±5) |
| 2-hydroxybenzylamino | 4-chlorobutyl | $10^{-4}$ | 47.5 (±8) |
| 3-hydroxybenzylamino | H | $10^{-5}$ | 99 (±15) |
| 3-hydroxybenzylamino | tetrahydropyran-2-yl | $10^{-4}$ | 105.1 (±21) |
| 3-hydroxybenzylamino | tetrahydrofuran-2-yl | $10^{-4}$ | 107 (±16) |
| 3-hydroxybenzylamino | 4-chlorobutyl | $10^{-4}$ | 102.5 (±18) |
| 3-hydroxybenzylamino | 1-ethoxyethyl | $10^{-4}$ | 108.2 (±18) |
| 4-hydroxybenzylamino | H | | n.a. |
| 4-hydroxybenzylamino | tetrahydropyran-2-yl | $10^{-4}$ | 25.3 (±9) |
| 4-hydroxybenzylamino | tetrahydrofuran-2-yl | $10^{-4}$ | 13 (±4) |

TABLE 6-continued

The effect of novel compounds on the betacyanin content in
*Amaranthus caudatus* cotyledon/hypocotyl explants

| Tested compound | | Concentration with highest activity (mol · l$^{-1}$) | Activity (%) [10$^{-5}$ mol · l$^{-1}$ BAP = 100%] |
|---|---|---|---|
| R6 | R9 | | |
| 4-hydroxybenzylamino | 4-chlorobutyl | 10$^{-4}$ | 33.4 (±8) |
| (E)-(4-hydroxy-3-methylbut-2-en-1-ylamino) | H | 10$^{-5}$ | 116 (±13) |
| (E)-(4-hydroxy-3-methylbut-2-en-1-ylamino) | tetrahydropyran-2-yl | 10$^{-4}$ | 299.4 (±14) |
| (E)-(4-hydroxy-3-methylbut-2-en-1-ylamino) | tetrahydrofuran-2-yl | 10$^{-4}$ | 117 (±7) |
| (E)-(4-hydroxy-3-methylbut-2-en-1-ylamino) | 4-chlorobutyl | 10$^{-4}$ | 123.8 (±12) |
| (E)-(4-hydroxy-3-methylbut-2-en-1-ylamino) | 1-ethoxyethyl | 10$^{-4}$ | 92.5 (±10) |
| 4-hydroxy-3-methylbutylamino | H | 10$^{-4}$ | 75 (±13) |
| 4-hydroxy-3-methylbutylamino | tetrahydropyran-2-yl | 10$^{-4}$ | 83 (±6) |
| 4-hydroxy-3-methylbutylamino | tetrahydrofuran-2-yl | 10$^{-4}$ | 80 (±7) |
| 4-hydroxy-3-methylbutylamino | 4-chlorobutyl | 10$^{-4}$ | 81 (±6) |
| 4-hydroxy-3-methylbutylamino | 1-ethoxyethyl | 10$^{-4}$ | 85 (±7) |
| 2-hydroxy-3-methoxybenzylamino* | H | 10$^{-4}$ | 19 (±3) |
| 2-hydroxy-3-methoxybenzylamino | tetrahydropyran-2-yl | 10$^{-4}$ | 32 (±7) |
| 2-hydroxy-3-methoxybenzylamino | 4-chlorobutyl | 10$^{-4}$ | 53 (±6) |
| 3,5-dihydroxybenzylamino* | H | 10$^{-5}$ | 53 (±9) |
| 3,5-dihydroxybenzylamino | tetrahydropyran-2-yl | 10$^{-5}$ | 53 (±9) |
| 2-hydroxy-4-methoxybenzylamino | tetrahydropyran-2-yl | 10$^{-4}$ | 37 (±6) |
| 2,5-dihydroxybenzylamino | tetrahydropyran-2-yl | 10$^{-4}$ | 35.1 (±9) |
| 3,4-dihydroxybenzylamino | tetrahydropyran-2-yl | 10$^{-4}$ | 52 (±13) |
| 4-hydroxy-3,5-dimethoxybenzylamino | tetrahydropyran-2-yl | 10$^{-4}$ | 8 (±3) |
| 4-hydroxy-2,6-dimethoxybenzylamino | tetrahydropyran-2-yl | 10$^{-4}$ | 12 (±5) |
| 4-hydroxy-3-methoxybenzylamino | tetrahydropyran-2-yl | 10$^{-4}$ | 57 (±11) |
| 3-hydroxy-4-methoxybenzylamino | tetrahydropyran-2-yl | 10$^{-4}$ | 41 (±7) |
| 2-hydroxy-3-methylbenzylamino | tetrahydropyran-2-yl | 10$^{-4}$ | 68.8 (±17) |
| 2-hydroxy-5-methylbenzylamino | tetrahydropyran-2-yl | 10$^{-4}$ | 68.4 (±11) |
| 4-hydroxy-3-methylbenzylamino | tetrahydropyran-2-yl | 10$^{-4}$ | 7 (±1) |
| 4-hydroxy-5-methylbenzylamino | tetrahydropyran-2-yl | 10$^{-4}$ | 5 (±3) |
| 3-hydroxyfurfurylamino | tetrahydropyran-2-yl | 10$^{-4}$ | 65 (±12) |
| 4-hydroxyfurfurylamino | tetrahydropyran-2-yl | 10$^{-4}$ | 115 (±18) |
| 2-hydroxyanilino | tetrahydropyran-2-yl | 10$^{-4}$ | 65 (±10) |
| 3-hydroxyanilino | tetrahydropyran-2-yl | 10$^{-4}$ | 122 (±11) |
| 4-hydroxyanilino | tetrahydropyran-2-yl | 10$^{-4}$ | 32 (±7) |
| 4-hydroxy-3-methylanilino | tetrahydropyran-2-yl | 10$^{-4}$ | 15 (±5) |
| 4-hydroxy-5-methylanilino | tetrahydropyran-2-yl | 10$^{-4}$ | 17 (±8) |
| 4-hydroxy-3,5-dimethoxyanilino | tetrahydropyran-2-yl | 10$^{-4}$ | 10 (±4) |
| 4-hydroxy-2,6-dimethoxyanilino | tetrahydropyran-2-yl | 10$^{-4}$ | 8 (±2) |
| 4-hydroxy-3,5-dimethoxybenzylamino | tetrahydrofuran-2-yl | 10$^{-4}$ | 2 (±1) |
| 4-hydroxy-2,6-dimethoxybenzylamino | tetrahydrofuran-2-yl | 10$^{-4}$ | 7 (±3) |
| 3-hydroxy-4-methoxybenzylamino | tetrahydrofuran-2-yl | 10$^{-4}$ | 32 (±9) |
| 4-hydroxy-3-methylbenzylamino | tetrahydrofuran-2-yl | 10$^{-4}$ | 2 (±0.7) |
| 4-hydroxy-5-methylbenzylamino | tetrahydrofuran-2-yl | 10$^{-4}$ | 22 (±6) |
| 4-hydroxyanilino | tetrahydrofuran-2-yl | 10$^{-4}$ | 22 (±6) |
| 4-hydroxy-3-methylanilino | tetrahydrofuran-2-yl | 10$^{-4}$ | 6 (±3) | n.a. means not active

*the control cytokinins described in Doležal et al. (Bioorg. Med.Chem. 14: 875, 2006).

Example 16

Testing of antisenescence properties of novel cytokinin compounds on wheat leaf segments. Seeds of winter wheat, *Triticum aestivum* cv. Hereward, were washed under running water for 24 hours and then sown on vermiculite soaked with the Knop's solution. They were placed in the grow chamber at 25° C. with a 16 h-8 h light period at 50 mmol.m$^{-2}$.s$^{-1}$. After 7 days, the first leaf was fully developed and the second leaf had started to grow. A 35 mm long tip section of the first leaf, was removed from each of 5 seedlings and trimmed slightly to a combined weight of 100 mg. The basal ends of the five leaf tips were placed in the wells of a microtiter polystyrene plate containing 150 ml of the solution of the tested compound each. The entire plate was inserted into a plastic box lined with paper tissues soaked with distilled water to prevent leaf sections from drying out. After 96 h incubation in the dark at 25° C., the leaves were removed and chlorophyll was extracted by heating at 80° C. for 10 min in 5 ml of 80% ethanol (v/v). The sample volume was then restored to 5 ml by the addition of 80% ethanol (v/v). The absorbance of the extract was recorded at 665 nm. In addition, chlorophyll extracts from fresh leaves and leaf tips incubated in deionized water were measured. From the obtained data, the concentration with the highest activity was selected for each compound tested. Relative activity of the compound at this concentration was calculated (Table 7). The activity obtained for $10^{-4}$ M 6-benzylaminopurine (BAP) was defined as 100%. The values shown are means of five replicates and the whole experiment was repeated twice.

The compounds to be tested were dissolved in dimethylsulfoxide (DMSO) and the solution brought up to $10^{-3}$ M with distilled water. This stock solution was further diluted with distilled water to a concentration ranging from $10^{-8}$ M to $10^{-4}$ M. The final concentration of DMSO did not exceed 0.2% and therefore did not affect the biological activity in the assay system used.

The compounds listed in Table 7 can be divided into 2 groups. The first group contains natural cytokinins, represented by $N^6$-substituted purines (compounds known in the prior art serving as controls). The second group contains the novel 6,9-disubstituted purines derived from the compounds of the first group. The results show that the substitution in position 9 of the purine skeleton generally led to an increase of the antisenescent activity in comparison to the corresponding classical cytokinins.

TABLE 7

The effect of novel compounds on the retention of chlorophyll in excised wheat leaf tips (standard deviations of the mean for 10 replicate determinations are shown)

| Tested compound | | concentration with highest activity | activity (%) |
|---|---|---|---|
| R6 | R9 | $(mol \cdot l^{-1})$ | $[10^{-4} \, mol \cdot l^{-1} \, BAP = 100\%]$ |
| benzylamino | H | $10^{-4}$ | 100 |
| benzylamino | tetrahydropyran-2-yl | $10^{-4}$ | 105 (±0.5) |
| 2-hydroxybenzylamino | H | $10^{-4}$ | 22.4 (±5) |
| 2-hydroxybenzylamino | tetrahydropyran-2-yl | $10^{-4}$ | 23.6 (±7) |
| 2-hydroxybenzylamino | tetrahydrofuran-2-yl | $10^{-4}$ | 26 (±2) |
| 2-hydroxybenzylamino | 4-chlorobutyl | $10^{-4}$ | 47.5 (±8) |
| 3-hydroxybenzylamino | H | $10^{-4}$ | 105.9 (±14) |
| 3-hydroxybenzylamino | tetrahydropyran-2-yl | $10^{-4}$ | 133.1 (±15) |
| 3-hydroxybenzylamino | tetrahydrofuran-2-yl | $10^{-4}$ | 113 (±18) |
| 3-hydroxybenzylamino | 4-chlorobutyl | $10^{-4}$ | 102.5 (±18) |
| 3-hydroxybenzylamino | 1-ethoxyethyl | $10^{-4}$ | 108.2 (±18) |
| 4-hydroxybenzylamino | H | | n.a. |
| 4-hydroxybenzylamino | tetrahydropyran-2-yl | $10^{-4}$ | 10.1 (±9) |
| 4-hydroxybenzylamino | tetrahydrofuran-2-yl | $10^{-4}$ | 3 (±1) |
| 4-hydroxybenzylamino | 4-chlorobutyl | $10^{-4}$ | 33.4 (±8) |
| (E)-(4-hydroxy-3-methylbut-2-en-1-ylamino) | H | $10^{-4}$ | 28.3 (±17) |
| (E)-(4-hydroxy-3-methylbut-2-en-1-ylamino) | tetrahydropyran-2-yl | $10^{-4}$ | 38.2 (±7) |
| (E)-(4-hydroxy-3-methylbut-2-en-1-ylamino) | tetrahydrofuran-2-yl | $10^{-4}$ | 45 (±6) |
| (E)-(4-hydroxy-3-methylbut-2-en-1-ylamino) | 4-chlorobutyl | $10^{-4}$ | 73.8 (±12) |
| (E)-(4-hydroxy-3-methylbut-2-en-1-ylamino) | 1-ethoxyethyl | $10^{-4}$ | 92.5 (±10) |
| 4-hydroxy-3-methylbutylamino | H | $10^{-4}$ | 89 (±11) |
| 4-hydroxy-3-methylbutylamino | tetrahydropyran-2-yl | $10^{-4}$ | 95 (±8) |
| 4-hydroxy-3-methylbutylamino | tetrahydrofuran-2-yl | $10^{-4}$ | 91 (±4) |
| 4-hydroxy-3-methylbutylamino | 4-chlorobutyl | $10^{-4}$ | 89 (±7) |
| 4-hydroxy-3-methylbutylamino | 1-ethoxyethyl | $10^{-4}$ | 94 (±10) |
| 2-hydroxy-3-methoxybenzylamino* | H | $10^{-4}$ | 34 (±5) |
| 2-hydroxy-3-methoxybenzylamino | tetrahydropyran-2-yl | $10^{-4}$ | 50 (±5) |
| 3,5-dihydroxybenzylamino* | H | $10^{-4}$ | 134 (±10) |
| 3,5-dihydroxybenzylamino | tetrahydropyran-2-yl | $10^{-4}$ | 145 (±12) |
| 2-hydroxy-4-methoxybenzylamino | tetrahydropyran-2-yl | $10^{-4}$ | 35 (±9.5) |
| 2,5-dihydroxybenzylamino | tetrahydropyran-2-yl | $10^{-4}$ | 15 (±5) |
| 3,4-dihydroxybenzylamino | tetrahydropyran-2-yl | $10^{-4}$ | 71.3 (±17) |
| 4-hydroxy-3,5-dimethoxybenzylamino | tetrahydropyran-2-yl | $10^{-4}$ | 42 (±13) |
| 4-hydroxy-2,6-dimethoxybenzylamino | tetrahydropyran-2-yl | $10^{-4}$ | 22 (±4) |
| 4-hydroxy-3-methoxybenzylamino | tetrahydropyran-2-yl | $10^{-4}$ | 55 (±18) |
| 3-hydroxy-4-methoxybenzylamino | tetrahydropyran-2-yl | $10^{-4}$ | 47 (±11) |
| 2-hydroxy-3-methylbenzylamino | tetrahydropyran-2-yl | $10^{-4}$ | 16.4 (±3) |
| 2-hydroxy-5-methylbenzylamino | tetrahydropyran-2-yl | $10^{-4}$ | 82 (±12) |
| 4-hydroxy-3-methylbenzylamino | tetrahydropyran-2-yl | $10^{-4}$ | 9 (±2) |
| 4-hydroxy-5-methylbenzylamino | tetrahydropyran-2-yl | $10^{-4}$ | 3 (±1) |
| 3-hydroxyfurfurylamino | tetrahydropyran-2-yl | $10^{-4}$ | 45 (±13) |
| 4-hydroxyfurfurylamino | tetrahydropyran-2-yl | $10^{-4}$ | 101 (±17) |
| 2-hydroxyanilino | tetrahydropyran-2-yl | $10^{-4}$ | 11 (±4) |
| 3-hydroxyanilino | tetrahydropyran-2-yl | $10^{-4}$ | 23 (±7) |
| 4-hydroxy-3-methylanilino | tetrahydropyran-2-yl | $10^{-4}$ | 7 (±5) |
| 4-hydroxy-5-methylanilino | tetrahydropyran-2-yl | $10^{-4}$ | 10 (±3) |
| 4-hydroxy-3,5-dimethoxyanilino | tetrahydropyran-2-yl | $10^{-4}$ | 28 (±9) |
| 4-hydroxy-2,6-dimethoxyanilino | tetrahydropyran-2-yl | $10^{-4}$ | 14 (±4) |

TABLE 7-continued

The effect of novel compounds on the retention of chlorophyll in excised wheat leaf tips (standard deviations of the mean for 10 replicate determinations are shown)

| Tested compound | | concentration with highest activity | activity (%) |
|---|---|---|---|
| R6 | R9 | (mol · l$^{-1}$) | [10$^{-4}$ mol · l$^{-1}$ BAP = 100%] |
| 4-hydroxy-3,5-dimethoxybenzylamino | tetrahydrofuran-2-yl | 10$^{-4}$ | 36 (±10) |
| 4-hydroxy-2,6-dimethoxybenzylamino | tetrahydrofuran-2-yl | 10$^{-4}$ | 14 (±5) |
| 3-hydroxy-4-methoxybenzylamino | tetrahydrofuran-2-yl | 10$^{-4}$ | 35 (±8) |
| 4-hydroxy-3-methylbenzylamino | tetrahydrofuran-2-yl | 10$^{-4}$ | 1.4 (±2) |
| 4-hydroxy-5-methylbenzylamino | tetrahydrofuran-2-yl | 10$^{-4}$ | 17 (±5) |
| 4-hydroxyanilino | tetrahydrofuran-2-yl | 10$^{-4}$ | 28 (±4) |
| 4-hydroxy-3-methylanilino | tetrahydrofuran-2-yl | 10$^{-4}$ | 4 (±3) |

*the control cytokinins described in Doležal et al. (Bioorg. Med.Chem. 14: 875, 2006)

Example 17

Inhibition of aging of normal human cells by novel compounds. In this example, human diploid fibroblasts (HCA cells of various passage levels: passage 20—designated HCA20; passage 40—designated HCA40; passage 60—designated HCA60) were stained for β-galactosidase activity. The medium used for the cell cultivation was removed, the cells were washed twice in PNS, and fixed in 2-3 ml of fixing solution comprised of a 2% formaldehyde and 0.2% glutaraldehyde in PBS. The cells were incubated at room temperature for 5 minutes, and then washed twice with PBS. The cells were subsequently incubated at 37° C. (without $CO_2$) for 16 hours in 2-3 ml of the solution comprising potassium ferricyanide (5 mM), potassium ferrocyanide (5 mM), $MgCl_2$ (2 mM), X-gal (5-bromo-4-chloro-3-indolyl-β-D-galactopyranoside) (1 mg/ml), in citric/phosphate buffer, pH 6.0) Following this incubation period, the cell samples were observed in order to detect the presence of blue cells, indicating that X-gal had been cleaved (positively senescent cells). In this experiment, senescent cells, but no other cells were stained blue due to the action of β-galactosidase on the substrate.

TABLE 8

The effect of novel compounds on the number of senescent cells in the culture of human fibroblasts

| Substituent | | SENESCENT CELLS (%) | | |
|---|---|---|---|---|
| R6 | R9 | HCA20 | HCA40 | HCA60 |
| benzylamino | tetrahydropyran-2-yl | 3 | 4 | 47 |
| (Z)-(4-hydroxy-3-methylbut-2-en-1-ylamino) | tetrahydropyran-2-yl | 4 | 5 | 15 |
| 4-hydroxy-3-methylbutylamino | tetrahydropyran-2-yl | 5 | 2 | 25 |
| 2-hydroxybenzylamino | tetrahydropyran-2-yl | 4 | 2 | 26 |
| 3-hydroxybenzylamino | tetrahydropyran-2-yl | 5 | 3 | 25 |
| 4-hydroxybenzylamino | tetrahydropyran-2-yl | 5 | 5 | 16 |
| 2-hydroxy-3-methoxybenzylamino | tetrahydropyran-2-yl | 3 | 3 | 25 |
| 2-hydroxy-4-methoxybenzylamino | tetrahydropyran-2-yl | 3 | 4 | 27 |
| 3,4-dihydroxybenzylamino | tetrahydropyran-2-yl | 3 | 4 | 15 |
| 4-hydroxy-3,5-dimethoxybenzylamino | tetrahydropyran-2-yl | 4 | 5 | 17 |
| 4-hydroxy-2,6-dimethoxybenzylamino | tetrahydropyran-2-yl | 4 | 5 | 21 |
| 4-hydroxy-3-methoxybenzylamino | tetrahydropyran-2-yl | 4 | 4 | 19 |
| 3-hydroxy-4-methoxybenzylamino | tetrahydropyran-2-yl | 5 | 7 | 29 |
| 2-hydroxy-3-methylbenzylamino | tetrahydropyran-2-yl | 4 | 6 | 30 |
| 2-hydroxy-5-methylbenzylamino | tetrahydropyran-2-yl | 5 | 4 | 30 |
| 4-hydroxy-3-methylbenzylamino | tetrahydropyran-2-yl | 4 | 6 | 22 |
| 4-hydroxy-5-methylbenzylamino | tetrahydropyran-2-yl | 3 | 4 | 20 |
| 3-hydroxyfurfurylamino | tetrahydropyran-2-yl | 4 | 4 | 18 |
| 4-hydroxyfurfurylamino | tetrahydropyran-2-yl | 4 | 4 | 16 |
| 5-hydroxyfurfurylamino | tetrahydropyran-2-yl | 4 | 7 | 24 |
| 2-hydroxyanilino | tetrahydropyran-2-yl | 4 | 6 | 29 |
| 3-hydroxyanilino | tetrahydropyran-2-yl | 5 | 4 | 28 |
| 4-hydroxyanilino | tetrahydropyran-2-yl | 4 | 6 | 16 |
| 4-hydroxy-3-methylanilino | tetrahydropyran-2-yl | 3 | 4 | 19 |
| 4-hydroxy-5-methylanilino | tetrahydropyran-2-yl | 4 | 4 | 18 |
| 4-hydroxy-3,5-dimethoxyanilino | tetrahydropyran-2-yl | 4 | 5 | 22 |
| 4-hydroxy-2,6-dimethoxyanilino | tetrahydropyran-2-yl | 4 | 6 | 24 |
| 3-hydroxy-4-methoxyanilino | tetrahydropyran-2-yl | 5 | 4 | 28 |
| (Z)-(4-hydroxy-3-methylbut-2-en-1-ylamino) | tetrahydrofuran-2-yl | 4 | 5 | 15 |
| 4-hydroxy-3-methylbutylamino | tetrahydrofuran-2-yl | 5 | 2 | 25 |
| 2-hydroxybenzylamino | tetrahydrofuran-2-yl | 4 | 2 | 26 |

TABLE 8-continued

The effect of novel compounds on the number of senescent cells in the culture of human fibroblasts

| Substituent | | SENESCENT CELLS (%) | | |
|---|---|---|---|---|
| R6 | R9 | HCA20 | HCA40 | HCA60 |
| 3-hydroxybenzylamino | tetrahydrofuran-2-yl | 5 | 3 | 25 |
| 4-hydroxybenzylamino | tetrahydrofuran-2-yl | 5 | 5 | 16 |

As shown in Table 8, with an increasing number of passages, the staining became darker. For the oldest cells, there were only blue cells ranging from bright blue to almost opaque color. 6,9-Disubstituted purine derivatives were very effective in comparison to 6-(benzylamino)-9-(tetrahydropyran-2-yl)purine in retaining much lower level of senescent cells after 60 passages. In the case of long-standing cultivation the cells treated with the compounds of the invention were able to live for a 30% longer period than the control cells.

Example 18

In vitro cytotoxic activity of novel compounds. Low cytotoxicity of the compounds is the major property determining their cosmetic use. One of the parameters used, as the basis for cytotoxicity assays, is the metabolic activity of viable cells. For example, a microtiter assay, which uses the Calcein AM, is now widely used to quantify cell proliferation and cytotoxicity. For instance, this assay is used in drug screening programs and in chemosensitivity testing. Because only metabolically active cells cleave Calcein AM, these assays detect viable cells exclusively. The quantity of reduced Calcein AM corresponds to the number of vital cells in the culture.

Human T-lymphoblastic leukemia cell line CEM; promyelocytic HL-60 and monocytic U937 leukemias; breast carcinoma cell lines MCF-7, BT549, MDA-MB-231; glioblastoma U87MG cells; cervical carcinoma cells HELA; sarcoma cells U2OS and Saos2; hepatocellular carcinoma HepG2; mouse fibroblasts NIH3T3; mouse immortalized bone marrow macrophages B2.4 and B10A.4; P388D1 and L1210 leukemia; B16 and B16F10 melanomas; human osteosarcoma HOS; human myeloid leukemia K-562; human skin melanoma G-361 were used for routine screening of compounds. The cells were maintained in Nunc/Corning 80 cm$^2$ plastic tissue culture flasks and cultured in cell culture medium (DMEM with 5 g/l glucose, 2 mM glutamine, 100 U/ml penicillin, 100 mg/ml streptomycin, 10% fetal calf serum and sodium bicarbonate).

The cell suspensions that were prepared and diluted according to the particular cell type and the expected target cell density (2,500-30,000 cells per well based on cell growth characteristics) were added by pipette (80 ml) into 96-well microtiter plates. Inoculates were allowed a pre-incubation period of 24 hours at 37° C. and 5% $CO_2$ for stabilization. Four-fold dilutions of the intended test concentration were added at time zero in 20 ml aliquots to the microtiter plate wells. Usually, the compound tested was evaluated at six 4-fold dilutions. In routine testing, the highest well concentration was 166.7 mM, but it can be changed depending on the agent. All drug concentrations were examined in duplicate. Incubations of cells with the tested compounds lasted for 72 hours at 37° C., in a 5% $CO_2$ atmosphere and 100% humidity. At the end of the incubation period, the cells were assayed by using Calcein AM. Ten microliters of the stock solution were pipetted into each well and incubated for 1 hour. Fluorescence (FD) was measured with the Labsystem FIA Reader Fluoroscan Ascent (UK). The tumor cell survival ($GI_{50}$) was calculated using the following calculation: TCS= ($FD_{drug\ exposed\ well}$/mean $FD_{control\ wells}$)×100%. The $GI_{50}$ value, the drug concentration lethal to 50% of the tumor cells, was calculated from the obtained dose response curves.

Zero cytotoxicity of the novel compounds is the basic prerequisite for cosmetic applications. The cytotoxicity of the novel compounds was tested on a panel of cell lines of different histogenetic and species origin (Table 9). We show herein that equal activities were found in all tumor cell lines tested, however, the non-malignant cells, e.g., NIH3T3 fibroblasts and normal human lymphocytes, were resistant to 6,9-disubstituted purine induced cytotoxicity. The compounds listed in Table 9 can be divided into 2 groups. The first group contains "classical cytokinins" represented by 6-substituted purines (which are known in the prior art). The second group contains the novel 6,9-disubstituted derivatives of these compounds. The results show that the substitution in position 9 of the purine skeleton by tetrahyropyranyl or tetrahydrofuranyl group generally led to a decrease in the cytotoxic activity in comparison to the "classical cytokinin" analogues. As demonstrated in Table 9, $GI_{50}$ for NIH3T3 fibroblasts and normal human lymphocytes was always higher than 166.7 mM. The novel derivatives show no toxicity to normal and tumor cells in concentrations of about 166.7 mM and thus are more suitable for cosmetic applications than natural cytokinins (6-substituted purine derivatives) and the control substance 6-benzylamino-9-(tetrahydropyran-2-yl)purine.

TABLE 9

Cytotoxicity of novel compounds for different cancer cell lines

| | | Cell line tested/$GI_{50}$ (µmol/L) | | | | | |
|---|---|---|---|---|---|---|---|
| R6 | R9 | HOS | K-562 | MCF7 | NIH-3T3 | CEM | HL60 |
| furfurylamino | H | >166.7 | 164.1 | >166.7 | >166.7 | 155.1 | 148.7 |
| isopentenylamino | H | >166.7 | 146.9 | >166.7 | >166.7 | 92.2 | >166.7 |
| benzylamino | H | >166.7 | 138.9 | 166.1 | >166.7 | >166.7 | >166.7 |

TABLE 9-continued

Cytotoxicity of novel compounds for different cancer cell lines

| | | Cell line tested/GI$_{50}$ (μmol/L) | | | | | |
|---|---|---|---|---|---|---|---|
| R6 | R9 | HOS | K-562 | MCF7 | NIH-3T3 | CEM | HL60 |
| (E)-(4-hydroxy-3-methylbut-2-en-1-ylamino) | H | >166.7 | >166.7 | >166.7 | >166.7 | >166.7 | >166.7 |
| 3-hydroxybenzylamino | H | >166.7 | 128.4 | >166.7 | >166.7 | 90.1 | 79.2 |
| 2-hydroxybenzylamino | H | >166.7 | >166.7 | >166.7 | >166.7 | 69.2 | 78 |
| benzylamino | tetrahydropyran-2-yl | >166.7 | 123.4 | 158.2 | >166.7 | >166.7 | 163.4 |
| (E)-(4-hydroxy-3-methylbut-2-en-1-ylamino) | tetrahydropyran-2-yl | >166.7 | | >166.7 | >166.7 | >166.7 | >166.7 |
| 4-hydroxybenzylamino | tetrahydropyran-2-yl | >166.7 | | >166.7 | >166.7 | >166.7 | >166.7 |
| 2-hydroxy-5-methoxybenzylamino | tetrahydropyran-2-yl | >166.7 | >166.7 | >166.7 | >166.7 | >166.7 | >166.7 |
| 3-hydroxy-4-methoxybenzylamino | tetrahydropyran-2-yl | >166.7 | | >166.7 | >166.7 | | >166.7 |
| 4-hydroxy-3-methylbenzylamino | tetrahydropyran-2-yl | >166.7 | | >166.7 | >166.7 | >166.7 | >166.7 |
| 4-hydroxy-5-methylbenzylamino | tetrahydropyran-2-yl | >166.7 | | >166.7 | >1667 | >166.7 | >1667 |
| 4-hydroxyfurfurylamino | tetrahydropyran-2-yl | >166.7 | >166.7 | >166.7 | >166.,7 | | >166.,7 |
| 4-hydroxy-3-methylanilino | tetrahydropyran-2-yl | >166.7 | | >166.7 | >166.7 | | >166.7 |
| 4-hydroxy-5-methylanilino | tetrahydropyran-2-yl | >166.7 | | >166.7 | >166.7 | | >166.7 |
| 2,4-dihydroxyanilino | tetrahydropyran-2-yl | >166.7 | | >166.7 | >166.7 | | >166.7 |
| (E)-(4-hydroxy-3-methylbut-2-en-1-ylamino) | tetrahydrofuran-2-yl | >166.7 | | >166.7 | >166.7 | | >166.7 |
| 4-hydroxybenzylamino | tetrahydrofuran-2-yl | >166.7 | | >166.7 | >166.7 | | >166.7 |
| (E)-(4-hydroxy-3-methylbut-2-en-1-ylamino) | 4-chlorobutyl | >166.7 | | >166.7 | >166.7 | | >166.7 |
| 4-hydroxybenzylamino | 4-chlorobutyl | >166.7 | | >166.7 | >166.7 | | >166.7 |
| (E)-(4-hydroxy-3-methylbut-2-en-1-ylamino) | 1-ethoxyeth-2-yl | >166.7 | | >166.7 | >166.7 | | >166.7 |
| 4-hydroxybenzylamino | 1-ethoxyeth-2-yl | >166.7 | | >166.7 | >166.7 | | >166.7 |

Example 19

Immunosuppressive activity. Compounds having the ability to selectively inhibit lymphocyte proliferation are potent immunosuppressants which can be also used with advantage in cosmetic applications. One of the most important parameters of specific cellular immunity is the proliferative response of lymphocytes to antigens or polyclonal mitogens. The majority of normal mammalian peripheral lymphocytes are resting cells. Antigens or nonspecific polyclonal mitogens have the capacity to activate lymphoid cells and this is accompanied by dramatic changes of intracellular metabolism (mitochondrial activity, protein synthesis, nucleic acids synthesis, formation of blastic cells and cellular proliferation). A variety of in vitro assays has been developed to measure the proliferative response of lymphocytes. The most commonly used one is the $^3$H-thymidine incorporation method.

During the cell proliferation, DNA must to be replicated before the cell divides into two daughter cells. This close association between cell doubling and DNA synthesis is very attractive for assessing the cell proliferation. If labeled DNA precursors are added to the cell culture, the cells that are about to divide incorporate the labeled nucleotide into their DNA. Traditionally, those assays usually involve the use of radiolabeled nucleosides, particularly tritiated thymidine ([$^3$H]-TdR). The amount of the [$^3$H]-TdR incorporated into the cellular DNA is quantified by liquid scintillation counting.

Human heparinized peripheral blood was obtained from healthy volunteers by cubital vein puncture. The blood was diluted in PBS (1:3) and mononuclear cells were separated by centrifugation in Ficoll-Hypaque density gradient (Pharmacia, 1.077 g/ml) at 2200 rpm for 30 minutes. Following centrifugation, lymphocytes were washed in PBS and resuspended in cell culture medium (RMPI 1640, 2 mM glutamine, 100 U/ml penicillin, 100 mg/ml streptomycin, 10% fetal calf serum and sodium bicarbonate).

The cells, diluted at the target density of 1,100,000 cells/ml, were added by pipette (180 ml) into 96/well microtiter plates. Four-fold dilutions of the intended test concentration were added at time zero in 20 ml aliquots to the microtiter plate wells. Usually, the tested compound was evaluated at six sequential 4-fold dilutions. In routine testing, the highest well concentration was 266.7 mM. All drug concentrations were examined in duplicate. All wells with the exception of unstimulated controls were activated with 50 ml of concanavalin A (25 mg/ml). Incubations of cells with the tested compound lasted for 72 hours at 37° C., in 5% $CO_2$ atmosphere and 100% humidity. At the end of the incubation period, the cells were assayed by using the [$^3$H]-TdR.

Cell cultures were incubated with 0.5 mCi (20 ml of stock solution 500 mCi/ml) per well for 6 hours at 37° C. and 5% $CO_2$. The automated cell harvester was used to lyse the cells in water and adsorb the DNA onto glass-fiber filters in the form of microtiter plates. The DNA, incorporating [$^3$H]-TdR was retained on the filter while unincorporated material passed through. The filters were dried at room temperature overnight and sealed into a sample bag with 10-12 ml of scintillant. The amount of the [$^3$H]-TdR present in each filter (in cpm) was determined by scintillation counting in the Betaplate liquid scintillation counter. The effective dose of the immunosuppressant (ED) was calculated using the following equation: ED=(CPM$_{drug\ exposed\ well}$/mean CPM$_{control\ wells}$)×100% (CPM=counts per minute). The ED$_{50}$ value, the drug concentration inhibiting proliferation of 50% of lymphocytes, was calculated from the obtained dose response curves.

To evaluate immunosuppressive activity of 6,9-disubstituted purines, their ability to inhibit polyclonal mitogen induced proliferation of normal human lymphocytes was analyzed (Table 10). Our data demonstrate that these compounds have only marginal activity on the $^3$H-thymidine incorporation, nonetheless, they efficiently inhibit proliferation of activated lymphocytes. The effective immunosuppressive dose of the novel derivatives under in vitro conditions was close to 1-20 mM. These results represent new discovery of biological activity of cytokinin derived compounds which might find an application in cosmetics.

TABLE 10

Immunosupressive activity of novel compounds.

| Tested compound | | Human lymphocytes $ED_{50}$ |
|---|---|---|
| R6 | R9 | (mM) |
| benzylamino | H | n.a. |
| 2-hydroxybenzylamino | H | 68 |
| 3-methylbut-2-en-1-ylamino | H | 79.5 |
| benzylamino | tetrahydropyran-2-yl | 44.7 |
| 2-hydroxybenzylamino | tetrahydropyran-2-yl | 4.5 |
| 2-hydroxy-3-methoxybenzylamino | tetrahydropyran-2-yl | 7 |
| 2-hydroxy-4-methoxybenzylamino | tetrahydropyran-2-yl | 4.2 |
| 3,4-dihydroxybenzylamino | tetrahydropyran-2-yl | 9.5 |
| 3,5-dihydroxybenzylamino | tetrahydropyran-2-yl | 18.7 |
| 2-hydroxy-3-methylbenzylamino | tetrahydropyran-2-yl | 2.2 |
| 2-hydroxy-5-methylbenzylamino | tetrahydropyran-2-yl | 6.4 |
| 2-hydroxybenzylamino | tetrahydrofuran-2-yl | 10.2 |
| 2-hydroxy-3,5-dimethoxybenzylamino | tetrahydrofuran-2-yl | 6.5 |
| 2-hydroxy-4-methoxybenzylamino | tetrahydrofuran-2-yl | 9.7 |
| 2-hydroxy-3-methylanilino | tetrahydrofuran-2-yl | 14.3 |
| 2-hydroxybenzylamino | 4-chlorobutyl | 6.7 |
| 2-hydroxy-3-methoxybenzylamino | 4-chlorobutyl | 9.2 |
| 2-hydroxy-4-methoxybenzylamino | 4-chlorobutyl | 8.3 |
| 3,4-dihydroxybenzylamino | 1-ethoxyethyl | 10.8 |
| 3,5-dihydroxybenzylamino | 1-ethoxyethyl | 21.4 | n.a. means not active

Example 20

Anti-inflammatory activity. The compounds of formula 1 having anti-inflammatory activities can be used as cosmetics for treating inflammation skin disorders as atopic dermatitis, lichen planus, hyperpigmentation and Herpes simplex lesions. From this reason, rat C6 glioma (ATCC No. CCL107) was cultivated as a monolayer in a serum-free chemically defined medium containing Ham's F10-minimal essential medium (1:1 v/v), 2 mM L-glutamine, 1% (v/v) minimal essential medium vitamins (100×), 1% (v/v) minimal essential medium nonessential amino acids (100×), 100U/ml penicillin, 100 mg/ml streptomycin and 30 nM sodium selenite. Incubation was performed at 37° C. in a humidified atmosphere. The assays were performed in the logarithmic growth phase at a density of $2.5 \times 10^5$ cells/cm$^2$. Intracellular cAMP synthesis was induced by addition of 5 mM (−)isoproterenol. After 30 min incubation at 37° C. the medium was removed and the cellular amount of cAMP was determined using the cAMP-enzyme immunoassay Amersham kit. The $I_{50}$ value was determined from a dose-response curve in duplicate. The effect of the novel 6,9-disubstituted purines was measured after simultaneous addition with isoproterenol. The classical cytokinins, known in the prior art, were inactive.

TABLE 11

Modulation of the activity of β-adrenergic receptors by substituted purines

| Tested compound | | |
|---|---|---|
| R6 | R9 | Effect |
| benzylamino | H | n.a. |
| 3-hydroxybenzylamino | H | n.a. |
| furfurylamino | H | n.a. |
| 4-hydroxybenzylamino | tetrahydropyran-2-yl | 1.8-fold activation |
| 3,4-dihydroxybenzylamino | tetrahydropyran-2-yl | 1.7-fold activation |
| 4-hydroxy-2,6-dimethoxybenzylamino | tetrahydropyran-2-yl | 1.3-fol activation |
| 4-hydroxy-3-methoxybenzylamino | tetrahydropyran-2-yl | 1.6-fold activation | n.a. means not active

As P2Y$_1$-like and A2 purinergic receptors, negatively and positively coupled to adenylate cyclase, respectively, are present in rat C6 glioma, it remains to be determined whether the modulation of the synthesis of cAMP is due to the inhibition of the activation of β-adrenergic receptors by isoproterenol, or due to the activation of purinergic receptors.

Example 21

Development and content of an ointment. An ointment formulation suitable for treating psoriatic skin disorders is described. The formulation components are given below (expressed in ingredient grams per 100 g ointment).

| | Ingredient/100 g |
|---|---|
| 6-(4-hydroxybenzyl)amino-9-(tetrahydropyran-2-yl)purin (pTTHP) | 1.0 g |
| butylhydroxytoluenum (Nipanox ™ BHT) | 0.2 g |
| butylparaben (Nipabutyl ™) | 0.2 g |
| diethylene glycol monoethyl ether (Transcutol ™ P) | 10.0 g |
| glycerol dibehenate (Compritol ™ 888 ATO) | 22.0 g |
| propylene glycol laurate (Lauroglycol ™ FCC) | 66.6 g |

The possible ointment consistency may be further modified by addition of vaselinum album. It is expected that the transdermal Transcutol™ P/Lauroglycol™ FCC system will increase the efficiency of pTTHP.

Example 22

Gel formulation. A gel formulation suitable for treating psoriatic skin disorders is described. The formulation components are given below (expressed in ingredient grams per 100 g gel).

| | Ingredient/100 g |
|---|---|
| 6-(4-hydroxybenzyl)amino-9-(tetrahydropyran-2-yl)purin (pTTHP) | 1.0 g |
| butylhydroxytoluenum (Nipanox ™ BHT) | 0.2 g |
| butylparaben (Nipabutyl ™) | 0.2 g |
| diethylene glycol monoethyl ether (Transcutol ™ P) | 10.0 g |
| silica colloidalis anhydrica (Zeopharm ™ 177) | 5.0 g |
| propylene glycol laurate (Lauroglycol ™ FCC) | 83.6 g |

The gel consistency may be additionally modified by addition of silica colloidalis anhydrica. It is again expected that the transdermal Transcutol™ P/Lauroglycol™ FCC system will increase the efficiency of pTTHP. Silica colloidalis anhydrica is expected to slow down the penetration of the active substance.

Example 23

Preparation procedure for an ointment to be applied topically to skin. Such an ointment formulation is as follows:

| | Ingredient/200 g |
|---|---|
| 6-(4-hydroxybenzyl)amino-9-(tetrahydropyran-2-yl)purin (pTTHP) | 2.0 g |
| butylhydroxytoluenum (Nipanox ™ BHT) | 0.4 g |
| butylparaben (Nipabutyl ™) | 0.4 g |
| diethylene glycol monoethyl ether (Transcutol ™ P) | 20.0 g |
| glycerol dibehenate (Compritol ™ 888 ATO) | 44.0 g |
| propylene glycol laurate (Lauroglycol ™ FCC) | 133.2 g |

Recommended Procedure:

Phase A—pTTHP (2 g) was dissolved in 20 g of (Transcutor™ P) while stirring continuously at room temperature in a first container. The dissolution process may be accelerated by heating the solution to a maximum temperature of 40° C.

Phase B—(Nipanox™ BHT) (0.4 g) and 0.4 g of (Nipabutyl™) were dissolved while stirring continuously in 133.2 g of (Laurogiycol™ FCC) at a temperature of approximately 70° C. in a second container. The clear oily solution is heated to a temperature of approximately 80° C. and 44 g of (Compritol™ 888 ATO) are melted in it while stirring continuously. The clear oily solution is cooled down to approximately 60° C.

As Phase B is cooled and with continuous stirring, Phase A is added. A whitish ointment-like substance is obtained and then filled into plastic containers (about 15 g ointment per container).

Example 24

Formulation of a composition for topical application to the skin. A composition for topical application to the skin contains the following ingredients:

| | Amount |
|---|---|
| 6-(4-hydroxybenzyl)amino-9-(tetrahydropyran-2-yl)purin (pTTHP) | 0.1% |
| Oil phase: | |
| Cetyl alcohol | 5.0% |
| Glyceryl monostearate | 15.0% |
| Sorbitan monooleate | 0.3% |
| Polysorbate 80 USP | 0.3% |
| Aqueous phase: | |
| Methylcellulose 100 cps | 1.0% |
| Methyl paraben | 0.25% |
| Propyl paraben | 0.15% |
| Purified water | q.s. to 100% |

Methyl paraben and propyl paraben were dissolved in hot water and subsequently methylcellulose was dispersed in the hot water. The mixture was chilled at 6° C. until the methylcellulose dissolved (aqueous phase). The aqueous phase was then heated to 72° C. and added to the oil phase at 70° C. while stirring continuously. pTHPP was added at a temperature of 35° C. and the resulting mixture was stirred continuously until dispersion. This composition can be applied to the skin on at least a daily basis until the desired skin-ameliorating (anti-ageing) effect is reached.

The invention claimed is:

1. A method for improving the cosmetic appearance of mammalian epidermal cells, said method comprising applying a cosmetic composition to the mammalian epidermal cells, wherein the cosmetic composition comprises an effective amount of one or more 6,9-disubstituted purine derivatives of the general formula 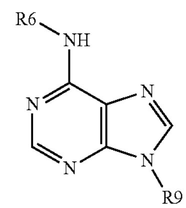 and their pharmaceutically acceptable salts, wherein the effective amount of the one or more 6,9-disubstituted purine derivatives or their pharmaceutically acceptable salts applied to the mammalian epidermal cells improves the cosmetic appearance of the mammalian epidermal cells;

wherein R6 is an alkyl, alkenyl, alkynyl, cycloalkyl, aryl, heterocycle, heterocycloalkyl, heteroalkyl, or arylalkyl group containing at least one hydroxyl substitution thereon, and wherein R9 is a tetrahydropyran-2-yl, tetrahydrofuran-2-yl, 4-chlorobutyl, or 1-ethoxyethyl group;

wherein alkyl denotes a branched or unbranched alkyl chain containing 1 to 8 carbon atoms, which is optionally substituted independently with 1 to 7 substituents selected from the group consisting of hydroxyl, halogen, alkyloxy, aryloxy, alkylamino, arylamino, amino, mercapto, carboxyl, cyano, nitro, carbamoyl, sulpho, sulphamido, acylamino, acyloxy, alkylthio, arylthio, cycloalkyl, alkyloxycarbonylamino, aryloxycarbonylamino, aryl, heterocycle, and heteroaryl;

wherein alkenyl denotes a branched or unbranched alkenyl chain containing 2 to 7 carbon atoms with at least one double bond therein, which is optionally substituted independently with 1 to 6 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group, wherein alkynyl denotes a branched or unbranched alkynyl chain containing 2 to 7 carbon atoms with at least one triple bond therein, which is optionally substituted independently with 1 to 6 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, alkyloxycarbonylamino, and aryloxycarbonylamino group;

wherein cycloalkyl denotes a monocyclic or polycyclic alkyl group containing 3 to 15 carbon atoms, which is optionally substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl aryloxycarbonylamino, and alkyloxycarbonylamino group;

wherein aryl denotes a aromatic carbocyclic group containing 6 to 18 carbon atoms with at least one aromatic ring or a multiple condensed ring with at least one aromatic ring, which is substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein heterocycle denotes a heterocyclic group containing 4 to 9 carbon atoms and at least one heteroatom selected from the group consisting of oxygen atom, sulphur atom, and nitrogen atom, which is optionally substituted independently at with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroaryl denotes a heterocycle in which at least one heterocyclic ring is aromatic, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heterocycloalkyl denotes a —$R_a$-Het group where Het is a heterocycle group and $R_a$ is an alkyl group, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroarylalkyl denotes a —$R_a$-HetAr group where HetAr is an heteroaryl group and $R_a$ is as defined above;

wherein arylalkyl denotes a —$R_b$—Ar group where Ar is aryl group and $R_b$ is a branched or unbranched alkyl chain containing 1 to 6 carbon atoms, which is optionally substituted independently with 1 to 5 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein halogen denotes a fluorine, bromine, chlorine, or iodine atom, wherein hydroxy denotes an —OH group, wherein mercapto denotes a —SH group, wherein amino denotes a —$NH_2$ group, wherein carbamoyl denotes a —$CONH_2$ group, wherein cyano denotes a —CN group, wherein carboxyl denotes a —COOH group, wherein nitro denotes a —$NO_2$ group, wherein sulpho denotes a —$SO_3R_c$ group where $R_c$ is hydrogen or alkyl, wherein sulphamido denotes the $SO_2NR_cR_c'$ group where $R_c$ and $R_c'$ are independently hydrogen or alkyl, wherein acyl denotes a —$C(O)R_d$ group, wherein $R_d$ is alkyl, aryl, arylalkyl or cycloalkyl, wherein acyloxy denotes a —O—$C(O)R_e$ group where $R_e$ is alkyl, aryl, or heterocycle, wherein acylamino denotes a —$NHCOR_f$ group, wherein $R_f$ is alkyl, heterocycle, or aryl, wherein alkyloxycarbonylamino denotes a —$NHCOOR_g$ group where $R_g$ is alkyl or cycloalkyl, wherein aryloxycarbonylamino denotes a —$NHCOOR_h$ group where $R_h$ is aryl, wherein alkyloxy denotes a —$OR_h$ group where $R_h$ is alkyl, cycloalkyl, or arylalkyl, wherein aryloxy denotes a —$OR_g$ group where $R_g$ is aryl, wherein alkylamino denotes a —$NR_iR_j$ group where $R_i$ is hydrogen, alkyl, or heterocycle and $R_j$ is alkyl or heterocycle, wherein arylamino denotes a —$NR_kR_h$ group where $R_k$ is hydrogen or aryl and $R_h$ is alkyl, aryl, or heterocycle, wherein alkylthio denotes a —$SR_h$ group where $R_h$ is as defined above, and wherein arylthio denotes a —$SR_g$ group where $R_g$ is as defined above.

2. The method as defined in claim 1, wherein the cosmetic composition further comprises one or more excipients and wherein the one or more 6,9-disubstituted purine derivatives are selected from the group consisting of 6-(2-hydroxycyclopropylamino)-9-(tetrahydropyran-2-yl, tetrahydrofuran-2-yl, 4-chlorobutyl, 1-ethoxyethyl)purine, 6-(3-hydroxycyclobutylamino)-9-(tetrahydropyran-2-yl, tetrahydrofuran-2-yl, 4-chlorobutyl, 1-ethoxyethyl)purine, 6-(4-hydroxycyclohexylamino)-9-(tetrahydropyran-2-yl, tetrahydrofuran-2-yl, 4-chlorobutyl, 1-ethoxyethyl)purine, 6-(2-hydroxy-3-chlorobenzylamino)-9-(tetrahydropyran-2-yl, tetrahydrofuran-2-yl, 4-chlorobutyl, 1-ethoxyethyl)purine, 6-(4-hydroxy-3-chlorobenzylamino)-9-(tetrahydropyran-2-yl, tetrahydrofuran-2-yl, 4-chlorobutyl, 1-ethoxyethyl)purine, 6-(3-hydroxy-4-chlorobenzylamino)-9-(tetrahydropyran-2-yl, tetrahydrofuran-2-yl, 4-chlorobutyl, 1-ethoxyethyl)purine, 6-(2-hydroxy-3-iodobenzylamino)-9-(tetrahydropyran-2-yl, tetrahydrofuran-2-yl, 4-chlorobutyl, 1-ethoxyethyl)purine, 6-(4-hydroxy-5-iodobenzylamino)-9-(tetrahydropyran-2-yl, tetrahydrofuran-2-yl, 4-chlorobutyl, 1-ethoxyethyl)purine, 6-(3-hydroxy-4-iodobenzylamino)-9-(tetrahydropyran-2-yl, tetrahydrofuran-2-yl, 4-chlorobutyl, 1-ethoxyethyl)purine, 6-(2-hydroxy-3-bromobenzylamino)-9-(tetrahydropyran-2-yl, tetrahydrofuran-2-yl, 4-chlorobutyl, 1-ethoxyethyl)purine, 6-(4-hydroxy-3-bromobenzylamino)-9-(tetrahydropyran-2-yl, tetrahydrofuran-2-yl, 4-chlorobutyl, 1-ethoxyethyl)purine, 6-(3-hydroxy-4-bromobenzylamino)-9-(tetrahydropyran-2-yl, tetrahydrofuran-2-yl, 4-chlorobutyl, 1-ethoxyethyl)purine, 6-(2-hydroxy-3-fluorobenzylamino)-9-(tetrahydropyran-2-yl, tetrahydrofuran-2-yl, 4-chlorobutyl, 1-ethoxyethyl)purine, 6-(4-hydroxy-3-fluorobenzylamino)-9-(tetrahydropyran-2-yl, tetrahydrofuran-2-yl, 4-chlorobutyl, 1-ethoxyethyl)purine, 6-(3-hydroxy-4-fluorobenzylamino)-9-(tetrahydropyran-2-yl, tetrahydrofuran-2-yl, 4-chlorobutyl, 1-ethoxyethyl)purine, 6-(2,3-dihydroxy-4-methoxybenzylamino)-9-(tetrahydropyran-2-yl, tetrahydrofuran-2-yl, 4-chlorobutyl, 1-ethoxyethyl)purine, 6-(2,4-dihydroxy-3-methoxybenzylamino)-9-(tetrahydropyran-2-yl, tetrahydrofuran-2-yl, 4-chlorobutyl, 1-ethoxyethyl)purine, 6-(2,5-dihydroxy-4-methoxybenzylamino)-9-(tetrahydropyran-2-yl, tetrahydrofuran-2-yl, 4-chlorobutyl, 1-ethoxyethyl)purine, 6-(3,5-dihydroxy-4-chlorobenzylamino)-9-(tetrahydropyran-2-yl, tetrahydrofuran-2-yl, 4-chlorobutyl, 1-ethoxyethyl)purine, 6-(2-hydroxybenzylamino)-9-(tetrahydropyran-2-yl, tetrahydrofuran-2-yl, 4-chlorobutyl, 1-ethoxyethyl)purine, 6-(3-hydroxybenzylamino)-9-(tetrahydropyran-2-yl, tetrahydrofuran-2-yl, 4-chlorobutyl, 1-ethoxyethyl)purine, 6-(4-hydroxybenzylamino)-9-(tetrahydropyran-2-yl, tetrahydrofuran-2-yl, 4-chlorobutyl, 1-ethoxyethyl)purine, 6-(3-hydroxy-4-methoxybenzylamino)-9-(tetrahydropyran-2-yl, tetrahydrofuran-2-yl, 4-chlorobutyl, 1-ethoxyethyl)purine, 6-(3-hydroxy-5-methoxybenzylamino)-9-(tetrahydropyran-2-yl, tetrahydrofuran-2-yl, 4-chlorobutyl, 1-ethoxyethyl)purine, 6-(2-hydroxy-3-methoxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(2-hydroxy-4-methoxybenzylamino)-9-(tetrahydropyran-2-yl, tetrahydrofuran-2-yl, 4-chlorobutyl, 1-ethoxyethyl)purine, 6-(4-hydroxy-2-methoxybenzylamino)-9-(tetrahydropyran-2-yl, tetrahydrofuran-2-yl, 4-chlorobutyl, 1-ethoxyethyl)purine, 6-(3,5-dimethyl-4-hydroxybenzylamino)-9-(tetrahydropyran-2-yl, tetrahydrofuran-2-yl, 4-chlorobutyl, 1-ethoxyethyl)purine, 6-(3,5-dibromo-4-hydroxybenzylamino)-9-(tetrahydropyran-2-yl, tetrahydrofuran-2-yl, 4-chlorobutyl, 1-ethoxyethyl)purine, 6-(3-hydroxymethyl-3-methylallyl)amino)-9-(tetrahydropyran-2-yl, tetrahydrofuran-2-yl, 4-chlorobutyl, 1-ethoxyethyl)purine, 6-(Z)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(Z)-(1''-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1''-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(2-hydroxy-3-pyridylamino)-9-(tetrahydropyran-2-yl, tetrahydrofuran-2-yl, 4-chlorobutyl, 1-ethoxyethyl)purine, 6-(3-hydroxy-4-pyridylamino)-9-(tetrahydropyran-2-yl, tetrahydrofuran-2-yl, 4-chlorobutyl, 1-ethoxyethyl)purine, 6-(2-hydroxy-4-morfolinylamino)-9-(tetrahydropyran-2-yl, tetrahydrofuran-2-yl, 4-chlorobutyl, 1-ethoxyethyl)purine, 6-(3-hydroxy-1-pyrrolidinylamino)-9-(tetrahydropyran-2-yl, tetrahydrofuran-2-yl, 4-chlorobutyl, 1-ethoxyethyl)purine, 6-(4-hydroxy-2-methylanilino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-6-methylanilino)-9-(tetrahydropyran-2-yl, tetrahydrofuran-2-yl, 4-chlorobutyl, 1-ethoxyethyl)purine, 6-(3-carboxy-4-hydroxyanilino)-9-(tetrahydropyran-2-yl, tetrahydrofuran-2-yl, 4-chlorobutyl, 1-ethoxyethyl)purine, 6-(4-hydroxy-2-methoxylanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine and their pharmaceutically acceptable salts.

3. The method defined in claim 1, wherein the cosmetic composition further comprises one or more excipients and wherein the one or more 6,9-disubstituted purine derivatives are selected from the group consisting of 6-(4-hydroxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1'-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine, and their pharmaceutically acceptable salts.

4. A method for improving the cosmetic appearance of mammalian skin in a mammal, said method comprising applying an effective amount of one or more 6,9-disubstituted purine derivatives of the general formula I, or their pharmaceutically acceptable salts,

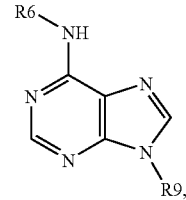

to the skin of the mammal;
wherein the effective amount of one or more 6,9-disubstituted purine derivatives or their pharmaceutically acceptable salts applied to the skin of the mammal improves the cosmetic appearance of the skin;
wherein R6 is an alkyl, alkenyl, alkynyl, cycloalkyl, aryl, heterocycle, heterocycloalkyl, heteroalkyl, or arylalkyl group containing at least one hydroxyl substitution thereon, and
wherein R9 is a tetrahydropyran-2-yl, tetrahydrofuran-2-yl, 4-chlorobutyl, or 1-ethoxyethyl group;
wherein alkyl denotes a branched or unbranched alkyl chain containing 1 to 8 carbon atoms, which is optionally substituted independently with 1 to 7 substituents selected from the group consisting of hydroxyl, halogen, alkyloxy, aryloxy, alkylamino, arylamino, amino, mercapto, carboxyl, cyano, nitro, carbamoyl, sulpho, sulphamido, acylamino, acyloxy, alkylthio, arylthio, cycloalkyl, alkyloxycarbonylamino, aryloxycarbonylamino, aryl, heterocycle, and heteroaryl;
wherein alkenyl denotes a branched or unbranched alkenyl chain containing 2 to 7 carbon atoms with at least one double bond therein, which is optionally substituted independently with 1 to 6 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group,
wherein alkynyl denotes a branched or unbranched alkynyl chain containing 2 to 7 carbon atoms with at least one trible bond therein, which is optionally substituted independently with 1 to 6 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, alkyloxycarbonylamino, and aryloxycarbonylamino group;

wherein cycloalkyl denotes a monocyclic or polycyclic alkyl group containing 3 to 15 carbon atoms, which is optionally substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl aryloxycarbonylamino, and alkyloxycarbonylamino group;

wherein aryl denotes a aromatic carbocyclic group containing 6 to 18 carbon atoms with at least one aromatic ring or a multiple condensed ring with at least one aromatic ring, which is substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein heterocycle denotes a heterocyclic group containing 4 to 9 carbon atoms and at least one heteroatom selected from the group consisting of oxygen atom, sulphur atom, and nitrogen atom, which is optionally substituted independently at with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroaryl denotes a heterocycle in which at least one heterocyclic ring is aromatic, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heterocycloalkyl denotes a —$R_a$-Het group where Het is a heterocycle group and $R_a$ is an alkyl group, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroarylalkyl denotes a —$R_a$-HetAr group where HetAr is an heteroaryl group and $R_a$ is as defined above;

wherein arylalkyl denotes a —$R_b$—Ar group where Ar is aryl group and $R_b$ is a branched or unbranched alkyl chain containing 1 to 6 carbon atoms, which is optionally substituted independently with 1 to 5 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein halogen denotes a fluorine, bromine, chlorine, or iodine atom, wherein hydroxy denotes an —OH group, wherein mercapto denotes a —SH group, wherein amino denotes a —$NH_2$ group, wherein carbamoyl denotes a —$CONN_2$ group, wherein cyano denotes a —CN group, wherein carboxyl denotes a —COON group, wherein nitro denotes a —$NO_2$ group, wherein sulpho denotes a —$SO_3R_c$ group where $R_c$ is hydrogen or alkyl, wherein sulphamido denotes the $SO_2NR_cR_c'$ group where $R_c$ and $R_c'$ are independently hydrogen or alkyl, wherein acyl denotes a —$C(O)R_d$ group, wherein $R_d$ is alkyl, aryl, arylalkyl or cycloalkyl, wherein acyloxy denotes a —O—$C(O)R_e$ group where $R_e$ is alkyl, aryl, or heterocycle, wherein acylamino denotes a —$NHCOR_f$ group, wherein $R_f$ is alkyl, heterocycle, or aryl, wherein alkyloxycarbonylamino denotes a —$NHCOOR_g$ group where $R_g$ is alkyl or cycloalkyl, wherein aryloxycarbonylamino denotes a —$NHCOOR_h$ group where $R_h$ is aryl, wherein alkyloxy denotes a —$OR_h$ group where $R_h$ is alkyl, cycloalkyl, or arylalkyl, wherein aryloxy denotes a —$OR_g$ group where $R_g$ is aryl, wherein alkylamino denotes a —$NR_iR_j$ group where $R_i$ is hydrogen, alkyl, or heterocycle and $R_j$ is alkyl or heterocycle, wherein arylamino denotes a —$NR_kR_h$ group where $R_k$ is hydrogen or aryl and $R_h$ is alkyl, aryl, or heterocycle, wherein alkylthio denotes a —$SR_h$ group where $R_h$ is as defined above, and wherein arylthio denotes a —$SR_g$ group where $R_g$ is as defined above.

5. The method of claim 4, wherein the one or more 6,9-disubstituted purine derivatives are selected from the group consisting of 6-(2-hydroxycyclopropylamino)-9-(tetrahydropyran-2-yl, tetrahydrofuran-2-yl, 4-chlorobutyl, 1-ethoxyethyl)purine, 6-(3-hydroxycyclobutylamino)-9-(tetrahydropyran-2-yl, tetrahydrofuran-2-yl, 4-chlorobutyl, 1-ethoxyethyl)purine, 6-(4-hydroxycyclohexylamino)-9-(tetrahydropyran-2-yl, tetrahydrofuran-2-yl, 4-chlorobutyl, 1-ethoxyethyl)purine, 6-(2-hydroxy-3-chlorobenzylamino)-9-(tetrahydropyran-2-yl, tetrahydrofuran-2-yl, 4-chlorobutyl, 1-ethoxyethyl)purine, 6-(4-hydroxy-3-chlorobenzylamino)-9-(tetrahydropyran-2-yl, tetrahydrofuran-2-yl, 4-chlorobutyl, 1-ethoxyethyl)purine, 6-(3-hydroxy-4-chlorobenzylamino)-9-(tetrahydropyran-2-yl, tetrahydrofuran-2-yl, 4-chlorobutyl, 1-ethoxyethyl)purine, 6-(2-hydroxy-3-iodobenzylamino)-9-(tetrahydropyran-2-yl, tetrahydrofuran-2-yl, 4-chlorobutyl, 1-ethoxyethyl)purine, 6-(4-hydroxy-5-iodobenzylamino)-9-(tetrahydropyran-2-yl, tetrahydrofuran-2-yl, 4-chlorobutyl, 1-ethoxyethyl)purine, 6-(3-hydroxy-4-iodobenzylamino)-9-(tetrahydropyran-2-yl, tetrahydrofuran-2-yl, 4-chlorobutyl, 1-ethoxyethyl)purine, 6-(2-hydroxy-3-bromobenzylamino)-9-(tetrahydropyran-2-yl, tetrahydrofuran-2-yl, 4-chlorobutyl, 1-ethoxyethyl)purine, 6-(4-hydroxy-3-bromobenzylamino)-9-(tetrahydropyran-2-yl, tetrahydrofuran-2-yl, 4-chlorobutyl, 1-ethoxyethyl)purine, 6-(3-hydroxy-4-bromobenzylamino)-9-(tetrahydropyran-2-yl, tetrahydrofuran-2-yl, 4-chlorobutyl, 1-ethoxyethyl)purine, 6-(2-hydroxy-3-fluorobenzylamino)-9-(tetrahydropyran-2-yl, tetrahydrofuran-2-yl, 4-chlorobutyl, 1-ethoxyethyl)purine, 6-(4-hydroxy-3-fluorobenzylamino)-9-(tetrahydropyran-2-yl, tetrahydrofuran-2-yl, 4-chlorobutyl, 1-ethoxyethyl)purine, 6-(3-hydroxy-4-fluorobenzylamino)-9-(tetrahydropyran-2-yl, tetrahydrofuran-2-yl, 4-chlorobutyl, 1-ethoxyethyl)purine, 6-(2,3-dihydroxy-4-methoxybenzylamino)-9-(tetrahydropyran-2-yl, tetrahydrofuran-2-yl, 4-chlorobutyl, 1-ethoxyethyl)purine, 6-(2,4-dihydroxy-3-methoxybenzylamino)-9-(tetrahydropyran-2-yl, tetrahydrofuran-2-yl, 4-chlorobutyl, 1-ethoxyethyl) purine, 6-(2,5-dihydroxy-4-methoxybenzylamino)-9-(tetrahydropyran-2-yl, tetrahydrofuran-2-yl, 4-chlorobutyl, 1-ethoxyethyl)purine, 6-(3,5-dihydroxy-4-chlorobenzylamino)-9-(tetrahydropyran-2-yl, tetrahydrofuran-2-yl, 4-chlorobutyl, 1-ethoxyethyl)purine, 6-(2-hydroxybenzylamino)-9-(tetrahydropyran-2-yl, tetrahydrofuran-2-yl, 4-chlorobutyl, 1-ethoxyethyl)purine, 6-(3-hydroxybenzylamino)-9-(tetrahydropyran-2-yl, tetrahydrofuran-2-yl, 4-chlorobutyl, 1-ethoxyethyl)purine, 6-(4-hydroxybenzylamino)-9-(tetrahydropyran-2-yl, tetrahydrofuran-2-yl, 4-chlorobutyl, 1-ethoxyethyl)purine, 6-(3-hydroxy-4-methoxybenzylamino)-9-(tetrahydropyran-2-yl, tetrahydrofuran-2-yl, 4-chlorobutyl, 1-ethoxyethyl)purine, 6-(3-hydroxy-5-methoxybenzylamino)-9-(tetrahydropyran-2-yl, tetrahydrofuran-2-yl, 4-chlorobutyl, 1-ethoxyethyl)purine, 6-(2-hydroxy-3-methoxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(2-hydroxy-4-methoxybenzylamino)-9-(tetrahydropyran-2-yl, tetrahydrofuran-2-yl, 4-chlorobutyl, 1-ethoxyethyl)purine, 6-(4-hydroxy-2-methoxybenzylamino)-9-(tetrahydropyran-2-yl, tetrahydrofuran-2-yl, 4-chlorobutyl, 1-ethoxyethyl)purine, 6-(3,5-dimethyl-4-hydroxybenzylamino)-9-(tetrahydropyran-2-yl, tetrahydrofuran-2-yl, 4-chlorobutyl, 1-ethoxyethyl)purine, 6-(3,5-dibromo-4-hydroxybenzylamino)-9-(tetrahydropyran-2-yl, tetrahydrofuran-2-yl, 4-chlorobutyl, 1-ethoxyethyl) purine, 4-chlorobutyl, 1-ethoxyethyl)purine, 6-(3-hydroxymethyl-3-methylallyl)amino)-9-(tetrahydropyran-2-yl, tetrahydrofuran-2-yl, 4-chlorobutyl, 1-ethoxyethyl) purine, 6-(Z)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(Z)-(1"-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1"-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(2-hydroxy-3-pyridylamino)-9-(tetrahydropyran-2-yl, tetrahydrofuran-2-yl, 4-chlorobutyl, 1-ethoxyethyl)purine, 6-(3-hydroxy-4-pyridylamino)-9-(tetrahydropyran-2-yl, tetrahydrofuran-2-yl, 4-chlorobutyl, 1-ethoxyethyl)purine, 6-(2-hydroxy-4-morfolinylamino)-9-(tetrahydropyran-2-yl, tetrahydrofuran-2-yl, 4-chlorobutyl, 1-ethoxyethyl)purine, 6-(3-hydroxy-1-pyrrolidinylamino)-9-(tetrahydropyran-2-yl, tetrahydrofuran-2-yl, 4-chlorobutyl, 1-ethoxyethyl)purine, 6-(4-hydroxy-2-methylanilino)-9-(tetrahydropyran-2-yl, tetrahydrofuran-2-yl, 4-chlorobutyl, 1-ethoxyethyl) purine, 6-(4-hydroxy-3-methylanilino)-9-(tetrahydropyran-2-yl, tetrahydrofuran-2-yl, 4-chlorobutyl, 1-ethoxyethyl) purine, 6-(4-hydroxy-6-methylanilino)-9-(tetrahydropyran-2-yl, tetrahydrofuran-2-yl, 4-chlorobutyl, 1-ethoxyethyl) purine, 6-(3-carboxy-4-hydroxyanilino)-9-(tetrahydropyran-2-yl, tetrahydrofuran-2-yl, 4-chlorobutyl, 1-ethoxyethyl)purine, 6-(4-hydroxy-2-methoxyanilino)-9-(tetrahydropyran-2-yl, tetrahydrofuran-2-yl, 4-chlorobutyl, 1-ethoxyethyl) purine, 6-(4-hydroxy-3-methoxyanilino)-9-(tetrahydropyran-2-yl, tetrahydrofuran-2-yl, 4-chlorobutyl, 1-ethoxyethyl)purine and their pharmaceutically acceptable salts.

6. The method of claim 4, wherein the one or more 6,9-disubstituted purine derivatives are selected from the group consisting of 6-(4-hydroxybenzylamino)-9-(tetrahydropyran-2-yl, tetrahydrofuran-2-yl, 4-chlorobutyl, 1-ethoxyethyl) purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1'-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1'-methyl-4-hydroxy-3-methylbutylamino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine, and their pharmaceutically acceptable salts.

7. A method for improving the cosmetic appearance of human skin, said method comprising applying an effective amount of one or more 6,9-disubstituted purine derivatives or their pharmaceutically acceptable salts to the human skin, wherein the one or more 6,9-disubstituted purine derivatives are of the general formula

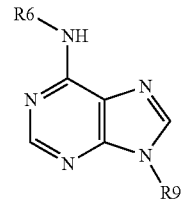

and their pharmaceutically acceptable salts,
wherein the effective amount of the one or more 6,9-disubstituted purine derivatives or their pharmaceutically acceptable salts improves the cosmetic appearance of the human skin,
wherein $R_6$ is an alkyl, alkenyl, alkynyl, cycloalkyl, aryl, heterocycle, heterocycloalkyl, heteroalkyl, or arylalkyl group containing at least one hydroxyl substitution thereon, and
wherein $R_9$ is a tetrahydropyran-2-yl, tetrahydrofuran-2-yl, 4-chlorobutyl, or 1-ethoxyethyl group;
wherein alkyl denotes a branched or unbranched alkyl chain containing 1 to 8 carbon atoms, which is optionally substituted independently with 1 to 7 substituents selected from the group consisting of hydroxyl, halogen, alkyloxy, aryloxy, alkylamino, arylamino, amino, mercapto, carboxyl, cyano, nitro, carbamoyl, sulpho, sulphamido, acylamino, acyloxy, alkylthio, arylthio, cycloalkyl, alkyloxycarbonylamino, aryloxycarbonylamino, aryl, heterocycle, and heteroaryl;

wherein alkenyl denotes a branched or unbranched alkenyl chain containing 2 to 7 carbon atoms with at least one double bond therein, which is optionally substituted independently with 1 to 6 substituents selected from the group containing halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group, wherein alkynyl denotes a branched or unbranched alkynyl chain containing 2 to 7 carbon atoms with at least one triple bond therein, which is optionally substituted independently with 1 to 6 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, alkyloxycarbonylamino, and aryloxycarbonylamino group;

wherein cycloalkyl denotes a monocyclic or polycyclic alkyl group containing 3 to 15 carbon atoms, which is optionally substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl aryloxycarbonylamino, and alkyloxycarbonylamino group;

wherein aryl denotes a aromatic carbocyclic group containing 6 to 18 carbon atoms with at least one aromatic ring or a multiple condensed ring with at least one aromatic ring, which is substituted independently with 1 to 7 substituents selected from the group consisting of halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein heterocycle denotes a heterocyclic group containing 4 to 9 carbon atoms and at least one heteroatom selected from the group consisting of oxygen atom, sulphur atom, and nitrogen atom, which is optionally substituted independently at with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroaryl denotes a heterocycle in which at least one heterocyclic ring is aromatic, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heterocycloalkyl denotes a —$R_a$-Het group where Het is a heterocycle group and $R_a$ is an alkyl group, which is optionally substituted independently with 1 to 7 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino, and alkyloxycarbonylamino group;

wherein heteroarylalkyl denotes a —$R_a$-HetAr group where HetAr is an heteroaryl group and $R_a$ is as defined above;

wherein arylalkyl denotes a —$R_b$—Ar group where Ar is aryl group and $R_b$ is a branched or unbranched alkyl chain containing 1 to 6 carbon atoms, which is optionally substituted independently with 1 to 5 substituents selected from the group consisting of alkyl, halogen, hydroxyl, alkyloxy, aryloxy, amino, alkylamino, arylamino, mercapto, carboxyl, cyano, nitro, carbamoyl, sulpho, sulphamido, acyl, acylamino, acyloxy, alkylthio, arylthio, cycloalkyl, aryloxycarbonylamino and alkyloxycarbonylamino group;

wherein halogen denotes a fluorine, bromine, chlorine, or iodine atom, wherein hydroxy denotes an —OH group, wherein mercapto denotes a —SH group, wherein amino denotes a —$NH_2$ group, wherein carbamoyl denotes a —$CONN_2$ group, wherein cyano denotes a —CN group, wherein carboxyl denotes a —COON group, wherein nitro denotes a —$NO_2$ group, wherein sulpho denotes a —$SO_3R_c$ group where $R_c$ is hydrogen or alkyl, wherein sulphamido denotes the $SO_2NR_cR_c'$ group where $R_c$ and $R_c'$ are independently hydrogen or alkyl, wherein acyl denotes a —$C(O)R_d$ group, wherein $R_d$ is alkyl, aryl, arylalkyl or cycloalkyl, wherein acyloxy denotes a —O—$C(O)R_e$ group where $R_e$ is alkyl, aryl, or heterocycle, wherein acylamino denotes a —$NHCOR_f$ group, wherein $R_f$ is alkyl, heterocycle, or aryl, wherein alkyloxycarbonylamino denotes a —$NHCOOR_g$ group where $R_g$ is alkyl or cycloalkyl, wherein aryloxycarbonylamino denotes a —$NHCOOR_h$ group where $R_h$ is aryl, wherein alkyloxy denotes a —$OR_h$ group where $R_h$ is alkyl, cycloalkyl, or arylalkyl, wherein aryloxy denotes a —$OR_g$ group where $R_g$ is aryl, wherein alkylamino denotes a —$NR_iR_j$ group where $R_i$ is hydrogen, alkyl, or heterocycle and $R_j$ is alkyl or heterocycle, wherein arylamino denotes a —$NR_kR_h$ group where $R_k$ is hydrogen or aryl and $R_h$ is alkyl, aryl, or heterocycle, wherein alkylthio denotes a —$SR_h$ group where $R_h$ is as defined above, and wherein arylthio denotes a —$SR_g$ group where $R_g$ is as defined above.

8. The method of claim 7, wherein the one or more 6,9-disubstituted purine derivatives or their pharmaceutically acceptable salts are selected from the group consisting of 6-(2-hydroxycyclopropylamino)-9-(tetrahydropyran-2-yl, tetrahydrofuran-2-yl, 4-chlorobutyl, 1-ethoxyethyl)purine, 6-(3-hydroxycyclobutylamino)-9-(tetrahydropyran-2-yl, tetrahydrofuran-2-yl, 4-chlorobutyl, 1-ethoxyethyl)purine, 6-(4-hydroxycyclohexylamino)-9-(tetrahydropyran-2-yl, tetrahydrofuran-2-yl, 4-chlorobutyl, 1-ethoxyethyl)purine, 6-(2-hydroxy-3-chlorobenzylamino)-9-(tetrahydropyran-2-yl, tetrahydrofuran-2-yl, 4-chlorobutyl, 1-ethoxyethyl)purine, 6-(4-hydroxy-3-chlorobenzylamino)-9-(tetrahydropyran-2-yl, tetrahydrofuran-2-yl, 4-chlorobutyl, 1-ethoxyethyl) purine, 6-(3-hydroxy-4-chlorobenzylamino)-9-(tetrahydropyran-2-yl, tetrahydrofuran-2-yl, 4-chlorobutyl, 1-ethoxyethyl)purine, 6-(2-hydroxy-3-iodobenzylamino)-9-(tetrahydropyran-2-yl, tetrahydrofuran-2-yl, 4-chlorobutyl, 1-ethoxyethyl)purine, 6-(4-hydroxy-5-iodobenzylamino)-9-(tetrahydropyran-2-yl, tetrahydrofuran-2-yl, 4-chlorobutyl, 1-ethoxyethyl)purine, 6-(3-hydroxy-4-iodobenzylamino)-9-(tetrahydropyran-2-yl, tetrahydrofuran-2-yl, 4-chlorobutyl, 1-ethoxyethyl)purine, 6-(2-hydroxy-3-bromobenzylamino)-9-(tetrahydropyran-2-yl, tetrahydrofuran-2-yl, 4-chlorobutyl, 1-ethoxyethyl)purine, 6-(4-hydroxy-3-bromobenzylamino)-9-(tetrahydropyran-2-yl, tetrahydrofuran-2-yl, 4-chlorobutyl, 1-ethoxyethyl)purine, 6-(3-hydroxy-4-bromobenzylamino)-9-(tetrahydropyran-2-yl, tetrahydrofuran-2-yl, 4-chlorobutyl, 1-ethoxyethyl)purine, 6-(2-hydroxy-3-fluorobenzylamino)-9-(tetrahydropyran-2-yl, tetrahydrofuran-2-yl, 4-chlorobutyl, 1-ethoxyethyl)purine, 6-(4-hydroxy-3-fluorobenzylamino)-9-(tetrahydropyran-2-yl, tetrahydrofuran-2-yl, 4-chlorobutyl, 1-ethoxyethyl)purine, 6-(3-hydroxy-4-fluorobenzylamino)-9-(tetrahydropyran-2-yl, tetrahydrofuran-2-yl, 4-chlorobutyl, 1-ethoxyethyl)purine, 6-(2,3-dihydroxy-4-methoxybenzylamino)-9-(tetrahydropyran-2-yl, tetrahydrofuran-2-yl, 4-chlorobutyl, 1-ethoxyethyl)purine, 6-(2,4-dihydroxy-3-methoxybenzylamino)-9-(tetrahydropyran-2-yl, tetrahydrofuran-2-yl, 4-chlorobutyl, 1-ethoxyethyl)purine, 6-(2,5-dihydroxy-4-methoxybenzylamino)-9-(tetrahydropyran-2-yl, tetrahydrofuran-2-yl, 4-chlorobutyl, 1-ethoxyethyl)purine, 6-(3,5-dihydroxy-4-chlorobenzylamino)-9-(tetrahydropyran-2-yl, tetrahydrofuran-2-yl, 4-chlorobutyl, 1-ethoxyethyl)purine, 6-(2-hydroxybenzylamino)-9-(tetrahydropyran-2-yl, tetrahydrofuran-2-yl, 4-chlorobutyl, 1-ethoxyethyl)purine, 6-(3-hydroxybenzylamino)-9-(tetrahydropyran-2-yl, tetrahydrofuran-2-yl, 4-chlorobutyl, 1-ethoxyethyl)purine, 6-(4-hydroxybenzylamino)-9-(tetrahydropyran-2-yl, tetrahydrofuran-2-yl, 4-chlorobutyl, 1-ethoxyethyl)purine, 6-(3-hydroxy-4-methoxybenzylamino)-9-(tetrahydropyran-2-yl, tetrahydrofuran-2-yl, 4-chlorobutyl, 1-ethoxyethyl)purine, 6-(3-hydroxy-5-methoxybenzylamino)-9-(tetrahydropyran-2-yl, tetrahydrofuran-2-yl, 4-chlorobutyl, 1-ethoxyethyl)purine, 6-(2-hydroxy-3-methoxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(2-hydroxy-4-methoxybenzylamino)-9-(tetrahydropyran-2-yl, tetrahydrofuran-2-yl, 4-chlorobutyl, 1-ethoxyethyl)purine, 6-(4-hydroxy-2-methoxybenzylamino)-9-(tetrahydropyran-2-yl, tetrahydrofuran-2-yl, 4-chlorobutyl, 1-ethoxyethyl)purine, 6-(3,5-dimethyl-4-hydroxybenzylamino)-9-(tetrahydropyran-2-yl, tetrahydrofuran-2-yl, 4-chlorobutyl, 1-ethoxyethyl)purine, 6-(3,5-dibromo-4-hydroxybenzylamino)-9-(tetrahydropyran-2-yl, tetrahydrofuran-2-yl, 4-chlorobutyl, 1-ethoxyethyl)purine, 4-chlorobutyl, 1-ethoxyethyl)purine, 6-(3-hydroxymethyl-3-methylallyl)amino)-9-(tetrahydropyran-2-yl, tetrahydrofuran-2-yl, 4-chlorobutyl, 1-ethoxyethyl)purine, 6-(Z)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(Z)-(1"-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1"-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1"-methyl-4-hydroxy-3-methylbutylamino)-9-(tetrahydropyran-2-yl, tetrahydrofuran-2-yl, 4-chlorobutyl, 1-ethoxyethyl)purine, 6-(2-hydroxy-3-pyridylamino)-9-(tetrahydropyran-2-yl, tetrahydrofuran-2-yl, 4-chlorobutyl, 1-ethoxyethyl)purine, 6-(3-hydroxy-4-pyridylamino)-9-(tetrahydropyran-2-yl, tetrahydrofuran-2-yl, 4-chlorobutyl, 1-ethoxyethyl)purine, 6-(2-hydroxy-4-morfolinylamino)-9-(tetrahydropyran-2-yl, tetrahydrofuran-2-yl, 4-chlorobutyl, 1-ethoxyethyl)purine, 6-(3-hydroxy-1-pyrrolidinylamino)-9-(tetrahydropyran-2-yl, tetrahydrofuran-2-yl, 4-chlorobutyl, 1-ethoxyethyl)purine, 6-(4-hydroxy-2-methylanilino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-6-methylanilino)-9-(tetrahydropyran-2-yl, tetrahydrofuran-2-yl, 4-chlorobutyl, 1-ethoxyethyl)purine, 6-(3-carboxy-4-hydroxyanilino)-9-(tetrahydropyran-2-yl, tetrahydrofuran-2-yl, 4-chlorobutyl, 1-ethoxyethyl)purine, 6-(4-hydroxy-2-methoxyanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine and their pharmaceutically acceptable salts.

9. The method of claim 7, wherein the one or more 6,9-disubstituted purine derivatives or their pharmaceutically acceptable salts are selected from the group consisting of 6-(4-hydroxybenzylamino)-9-(tetrahydropyran-2-yl, tetrahydrofuran-2-yl, 4-chlorobutyl, 1-ethoxyethyl)purine, 6-(4-hydroxy-3-methoxybenzylamino)-9-(tetrahydropyran-2-yl, tetrahydrofuran-2-yl, 4-chlorobutyl, 1-ethoxyethyl)purine, 6-(E)-(4-hydroxy-3-methylbut-2-en-1-ylamino)-9-(tetrahydropyran-2-yl, tetrahydrofuran-2-yl, 4-chlorobutyl, 1-ethoxyethyl)purine, 6-(E)-(1"-methyl-4-hydroxy-3-methylbut-2-en-1-ylamino)-9-(tetrahydropyran-2-yl, tetrahydrofuran-2-yl, 4-chlorobutyl, 1-ethoxyethyl)purine, 6-(4-hydroxy-3-methylbutylamino)-9-(tetrahydropyran-2-yl, tetrahydrofuran-2-yl, 4-chlorobutyl, 1-ethoxyethyl)purine, 6-(1"-methyl-4-hydroxy-3-methylbutylamino)-9-(tetrahydropyran-2-yl, tetrahydrofuran-2-yl, 4-chlorobutyl, 1-ethoxyethyl)purine, 6-(4-hydroxy-3-methylanilino)-9-(tetrahydropyran-2-yl, tetrahydrofuran-2-yl, 4-chlorobutyl, 1-ethoxyethyl)purine, 6-(4-hydroxy-3-methoxyanilino)-9-(tetrahydropyran-2-yl, tetrahydrofuran-2-yl, 4-chlorobutyl, 1-ethoxyethyl)purine, and their pharmaceutically acceptable salts.

10. The method of claim 1, wherein the one or more 6,9-disubstituted purine derivatives or their pharmaceutically acceptable salts are selected from the group consisting of 6-(2-hydroxybenzylamino)-9-tetrahydropyranylpurine, 6-(3-hydroxybenzylamino)-9-tetrahydropyranylpurine, 6-(2-methoxybenzylamino)-9-tetrahydropyranylpurine and their pharmaceutically acceptable salts and wherein the mammalian epidermal cells are human epidermal cells.

11. The method of claim 1, wherein the mammalian epidermal cells are human epidermal cells.

12. The method of claim 4, wherein the one or more 6,9-disubstituted purine derivatives or their pharmaceutically acceptable salts are selected from the group consisting of 6-(2-hydroxybenzylamino)-9-tetrahydropyranylpurine, 6-(3-hydroxybenzylamino)-9-tetrahydropyranylpurine, 6-(2-methoxybenzylamino)-9-tetrahydropyranylpurine and their pharmaceutically acceptable salts and wherein the mammalian skin is human skin.

13. The method of claim 4, wherein the mammalian skin is human skin.

14. The method of claim 7, wherein the one or more 6,9-disubstituted purine derivatives or their pharmaceutically acceptable salts are selected from the group consisting of 6-(2-hydroxybenzylamino)-9-tetrahydropyranylpurine, 6-(3-hydroxybenzylamino)-9-tetrahydropyranylpurine, 6-(2-methoxybenzylamino)-9-tetrahydropyranylpurine and their pharmaceutically acceptable salts.

\* \* \* \* \*